United States Patent
Gong et al.

(10) Patent No.: US 10,800,788 B2
(45) Date of Patent: Oct. 13, 2020

(54) 4-(ARYL)-N-(3-ALKOXYFURO[2,3-B]PYRAZIN-2-YL)-PIPERAZINE-1-CARBOXAMIDE DERIVATIVE AND ANTIPROLIFERATIVE EFFECT THEREOF

(71) Applicant: Dongguk University Industry-Academic Cooperation Foundation, Seoul (KR)

(72) Inventors: Young-Dae Gong, Seoul (KR); Soo-Youl Kim, Gyeonggi-do (KR); Eun Sil Lee, Seoul (KR); Tae-Sung Koo, Daejeon (KR); Nam-Sook Kang, Daejeon (KR); Na Yeon Kim, Gyeonggi-do (KR)

(73) Assignee: LSK NRDO CO., LTD., Seoul (KR)

( * ) Notice: Subject to any disclaimer, the term of this patent is extended or adjusted under 35 U.S.C. 154(b) by 0 days.

(21) Appl. No.: 16/308,028

(22) PCT Filed: Jun. 9, 2017

(86) PCT No.: PCT/KR2017/006004
§ 371 (c)(1),
(2) Date: Jul. 18, 2019

(87) PCT Pub. No.: WO2017/213452
PCT Pub. Date: Dec. 14, 2017

(65) Prior Publication Data
US 2019/0337959 A1 Nov. 7, 2019

(30) Foreign Application Priority Data
Jun. 9, 2016 (KR) .................. 10-2016-0071949
Jun. 8, 2017 (KR) .................. 10-2017-0071792

(51) Int. Cl.
*C07D 491/048* (2006.01)

(52) U.S. Cl.
CPC .................. *C07D 491/048* (2013.01)

(58) Field of Classification Search
CPC .................. C07D 491/048
See application file for complete search history.

(56) References Cited

U.S. PATENT DOCUMENTS 6,683,184 B2   1/2004   Cho et al.
8,314,100 B2   11/2012  Gong et al.

FOREIGN PATENT DOCUMENTS

| JP | 2002538153 A | 11/2002 |
| JP | 2008520653 A | 6/2008 |
| KR | 10-2001-0043018 A | 9/2003 |
| KR | 10-2014-0090500 A | 12/2014 |
| KR | 10-2016-0070005 A | 4/2017 |
| WO | 2006054830 A1 | 5/2006 |
| WO | 2011055115 A1 | 5/2011 |

OTHER PUBLICATIONS

Prichard. British Journal of Surgery, 2003, 90, 772-783 (Year: 2003).*
Kolli, Sunder Kumar et al. "NaSH in the construction of thiophene ring fused with N-heterocycles: A rapid and inexpensive synthesis of novel small molecules as potential inducers of apoptosis" Bioorganic & Medicinal Chemistry Letters 24 (2014) 4460-4465.
Ermolat'ev, Denis S. et al. "Ag+-Mediated Synthesis of Substituted Furo[2,3-b]pyrazines" SYNLETT 2007, No. 20, pp. 3117-3122.
Qin, Lijin et al. "Pd-catalyzed amidation of aryl(Het) halides with tert-butyl carbamate" Tetrahedron Letters 51 (2010) 4445-4448.
Routier, Sylvain et al. "A mild and selective method for N-Boc deprotection" Tetrahedron Letters 43 (2002) 589-591.

* cited by examiner

*Primary Examiner* — Noble E Jarrell
(74) *Attorney, Agent, or Firm* — Edwin S. Flores; Daniel J. Chalker; Chalker Flores, LLP

(57) ABSTRACT

The present invention relates to a novel 4-(aryl)-N-(3-alkoxyfuro[2,3-b]pyrazin-2-yl)-piperazine-1-carboxamide derivative compound useful in the prevention or treatment of cancer; a preparation method thereof; and a pharmaceutical composition comprising the same. The novel 4-(aryl)-N-(3-alkoxyfuro[2,3-b]pyrazin-2-yl)-piperazine-1-carboxamide derivative compound of the present invention can effectively inhibit the growth of proliferating cells, and thus can be useful in the prevention or treatment of cancer.

17 Claims, No Drawings

4-(ARYL)-N-(3-ALKOXYFURO[2,3-B]PYRAZIN-2-YL)-PIPERAZINE-1-CARBOXAMIDE DERIVATIVE AND ANTIPROLIFERATIVE EFFECT THEREOF

CROSS-REFERENCE TO RELATED APPLICATIONS

This application is the National Stage of International Application No. PCT/KR2017/006004, filed on Jun. 9, 2017 claiming the priority of KR 10-2016-0071949, filed on Jun. 9, 2016 and KR 10-2017-0071792, filed on Jun. 8, 2017, the content of each of which is incorporated by reference herein.

TECHNICAL FIELD OF THE INVENTION

The present invention relates to a novel 4-(aryl)-N-(3-alkoxyfuro[2,3-b]pyrazin-2-yl)-piperazine-1-carboxamide derivative compound useful in the prevention or treatment of cancer; a preparation method thereof; and a pharmaceutical composition comprising the same.

BACKGROUND OF THE INVENTION

Cancer is a serious disease which is the leading cause of death in Korea. Although numerous researches have been carried out in order to overcome cancer, it is considered as an incurable disease that is still required to be overcome. Cancer is a disease that occurs due to failing to regulate cell growth, thereby referring to a malignant tumor. Cancer cells uncontrollably divide and grow to form malignant tumors, which in turn invade adjacent tissues of the body. Additionally, cancer cells metastasize not only to adjacent tissues but also to distance tissues via lymphatic system or blood flow. Conventional treatments for cancer include surgery, chemotherapy, radiation therapy, etc. Among these treatments, chemotherapy using anticancer drugs is widely used for cancer treatment, and it is one of well-established treatment methods. These anticancer drugs intervene in the metabolic pathway of cancer cells to block the process of replication, transcription, and translation of DNA through the direct interaction with DNA; to interfere with the synthesis of nucleic acid precursors; and to inhibit cell division, thereby showing toxicity to cells. Accordingly, anticancer drugs cause fatal damage to normal cells, and as a result, the drugs have various side effects, for example, a reduction in the number of blood cells, such as white blood cells, platelets, erythrocytes, etc., due to marrow destruction; hair loss due to destruction of hair follicle cells; menstrual irregularity and male sterility due to side effects on ovaries and testicles; stomatitis, nausea-vomiting, swallowing difficulty and maldigestion due to destruction of mucosal cells in digestive organs; diarrhea; nephrotoxicity due to tubulorrhexis; peripheral neuritis and general weakness due to a neurological disorder; vascular disorders such as pain in blood vessels and rash and the like; discoloration of skins and nails; etc. Therefore, it is still required to develop an anticancer drug that can overcome side effects of anticancer drugs currently used in the clinic, reduce toxicity to normal cells, and can show effects on selective apoptosis of cancer cells.

In connection with such efforts, the present inventors have conducted prior invention searches, and noticed that a 1-[(2-methoxyquinoxalin-3-yl)aminocarbonyl]-4-arylpiperazine derivative has low toxicity while showing an excellent anticancer activity (U.S. Pat. No. 6,683,184). In addition, it was confirmed that since the 1-[(2-methoxyquinoxalin-3-yl) aminocarbonyl]-4-arylpiperazine derivative is a compound in which positions 5, 6, 7, and 8 of a quinoxaline ring are all substituted with hydrogen, there was a limit to the drug efficacy and the anticancer activity of cancer cells. Therefore, in order to overcome such limitation, the present inventors have developed a novel anticancer drug in which a substituent other than hydrogen is introduced at position 5 of the quinoxaline ring (U.S. Pat. No. 8,314,100).

SUMMARY OF THE INVENTION

Technical Problem

The present inventors have made intensive research efforts to find a novel compound having an anticancer activity, containing furo[2,3-b]pyrazine in addition to the quinoxaline in its parent structure. As a result, the present inventors have discovered a series of novel 4-(aryl)-N-(3-alkoxyfuro[2,3-b]pyrazin-2-yl)-piperazine-1-carboxamide derivative compounds, and confirmed that these compounds have an excellent effect of suppressing the growth and proliferation of cancer cells, thereby completing the present invention.

DETAILED DESCRIPTION OF THE INVENTION

Technical Solution

An object of the present invention is to provide a novel 4-(aryl)-N-(3-alkoxyfuro[2,3-b]pyrazin-2-yl)-piperazine-1-carboxamide derivative compound or a pharmaceutically acceptable salt thereof.

Another object of the present invention is to provide a method for preparing the compound.

A further object of the present invention is to provide a pharmaceutical composition for preventing or treating cancer, comprising the compound or the pharmaceutically acceptable salt thereof as an active ingredient.

A still further object of the present invention is to provide a method for preventing or treating a cancer disease from a subject, comprising a step of administering the pharmaceutical composition to a subject in need thereof.

Advantageous Effects

The novel 4-(aryl)-N-(3-alkoxyfuro[2,3-b]pyrazin-2-yl)-piperazine-1-carboxamide derivative compounds of the present invention can effectively suppress the growth of proliferating cells, and thus can be useful for the prevention or treatment of cancer.

Best Mode for Carrying Out the Invention

In order to overcome the above-mentioned problem, the present invention provides a compound represented by the following Formula 1 or a pharmaceutically acceptable salt thereof:

[Formula 1]

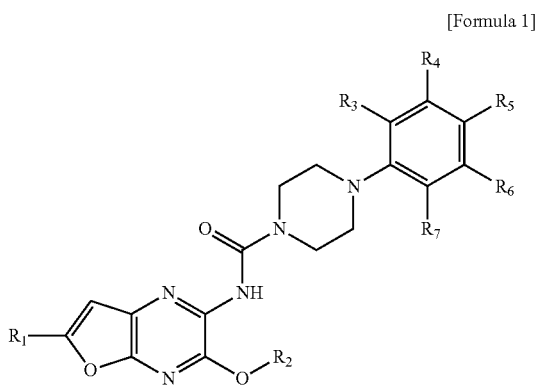

wherein $R_1$ is hydrogen, linear or branched $C_{1-6}$ alkyl, or halogen; $R_2$ is linear or branched $C_{1-6}$ alkyl; and $R_3$ to $R_7$ each independently represent hydrogen, halogen, linear or branched $C_{1-6}$ alkyl, linear or branched $C_{1-6}$ haloalkyl, $C_{1-6}$ alkoxy, $C_{1-6}$ haloalkoxy, ($C_{1-6}$ alkyl)amino($C_{1-6}$ alkoxy), or di($C_{1-6}$ alkyl)amino($C_{1-6}$ alkoxy).

For example, $R_1$ may be hydrogen, linear or branched $C_{1-6}$ alkyl, or halogen; $R_2$ may be linear or branched $C_{1-6}$ alkyl; $R_3$, $R_5$, and $R_7$ may all be hydrogen; and $R_4$ and $R_6$ may be the same or different from each other, and may each independently represent hydrogen, halogen, linear or branched $C_{1-6}$ alkyl, linear or branched $C_{1-6}$ haloalkyl, $C_{1-6}$ alkoxy, $C_{1-6}$ haloalkoxy, ($C_{1-6}$ alkyl)amino($C_{1-6}$ alkoxy), or di($C_{1-6}$ alkyl)amino($C_{1-6}$ alkoxy).

Preferably, $R_1$ may be hydrogen, methyl, or chloro.
Preferably, $R_2$ may be methyl or ethyl.
Preferably, $R_3$ to $R_7$ may each independently represent hydrogen, fluoro, methyl, trifluoromethyl, methoxy, trifluoromethoxy, or N,N-dimethylaminoethoxy.

Preferably, all of $R_3$, $R_5$, and $R_7$ may be hydrogen; $R_4$ and $R_6$ may be the same or different from each other, and may each independently represent hydrogen, fluoro, methyl, trifluoromethyl, methoxy, trifluoromethoxy, or N,N-dimethylaminoethoxy.

More preferably, $R_1$ may be hydrogen, methyl, or chloro; $R_2$ may be methyl or ethyl; $R_3$, $R_5$, and $R_7$ may all be hydrogen; and $R_4$ and $R_6$ may be the same of different from each other, and may each independently represent hydrogen, fluoro, methyl, trifluoromethyl, methoxy, trifluoromethoxy, or N,N-dimethylaminoethoxy, but these are not limited thereto.

Preferably, the compound represented by Formula 1 may be
1) 4-(3,5-dimethoxyphenyl)-N-(3-methoxyfuro[2,3-b]pyrazin-2-yl)piperazine-1-carboxamide,
2) 4-(3-methoxy-5-methylphenyl)-N-(3-methoxyfuro[2,3-b]pyrazin-2-yl)piperazine-1-carboxamide,
3) 4-(3-fluoro-5-methoxyphenyl)-N-(3-methoxyfuro[2,3-b]pyrazin-2-yl)piperazine-1-carboxamide,
4) 4-(3-(2-(dimethylamino)ethoxy)-5-methoxyphenyl)-N-(3-methoxyfuro[2,3-b]pyrazin-2-yl)piperazine-1-carboxamide,
5) 4-(3,5-dimethylphenyl)-N-(3-methoxyfuro[2,3-b]pyrazin-2-yl)piperazine-1-carboxamide,
6) 4-(3-fluoro-5-methylphenyl)-N-(3-methoxyfuro[2,3-b]pyrazin-2-yl)piperazine-1-carboxamide,
7) 4-(3,5-difluorophenyl)-N-(3-methoxyfuro[2,3-b]pyrazin-2-yl)piperazine-1-carboxamide,
8) 4-(3-fluoro-5-(trifluoromethyl)phenyl)-N-(3-methoxyfuro[2,3-b]pyrazin-2-yl)piperazine-1-carboxamide,
9) 4-(3,5-bis(trifluoromethyl)phenyl)-N-(3-methoxyfuro[2,3-b]pyrazin-2-yl)piperazine-1-carboxamide,
10) N-(3-methoxyfuro[2,3-b]pyrazin-2-yl)-4-(3-(trifluoromethoxy)phenyl)piperazine-1-carboxamide,
11) 4-(3,5-dimethoxyphenyl)-N-(3-ethoxyfuro[2,3-b]pyrazin-2-yl)piperazine-1-carboxamide,
12) N-(3-ethoxyfuro[2,3-b]pyrazin-2-yl)-4-(3-methoxy-5-methylphenyl)piperazine-1-carboxamide,
13) N-(3-ethoxyfuro[2,3-b]pyrazin-2-yl)-4-(3-fluoro-5-methoxyphenyl)piperazine-1-carboxamide,
14) 4-(3-(2-(dimethylamino)ethoxy)-5-methoxyphenyl)-N-(3-ethoxyfuro[2,3-b]pyrazin-2-yl)piperazine-1-carboxamide,
15) 4-(3,5-dimethylphenyl)-N-(3-ethoxyfuro[2,3-b]pyrazin-2-yl)piperazine-1-carboxamide,
16) N-(3-ethoxyfuro[2,3-b]pyrazin-2-yl)-4-(3-fluoro-5-methylphenyl)piperazine-1-carboxamide,
17) 4-(3,5-difluorophenyl)-N-(3-ethoxyfuro[2,3-b]pyrazin-2-yl)piperazine-1-carboxamide,
18) N-(3-ethoxyfuro[2,3-b]pyrazin-2-yl)-4-(3-fluoro-5-(trifluoromethyl)phenyl)piperazine-1-carboxamide,
19) 4-(3,5-bis(trifluoromethyl)phenyl)-N-(3-ethoxyfuro[2,3-b]pyrazin-2-yl)piperazine-1-carboxamide,
20) N-(3-ethoxyfuro[2,3-b]pyrazin-2-yl)-4-(3-(trifluoromethoxy)phenyl)piperazine-1-carboxamide,
21) 4-(3,5-dimethoxyphenyl)-N-(3-methoxy-6-methylfuro[2,3-b]pyrazin-2-yl)piperazine-1-carboxamide,
22) 4-(3-methoxy-5-methylphenyl)-N-(3-methoxy-6-methylfuro[2,3-b]pyrazin-2-yl)piperazine-1-carboxamide,
23) 4-(3-fluoro-5-methoxyphenyl)-N-(3-methoxy-6-methylfuro[2,3-b]pyrazin-2-yl)piperazine-1-carboxamide,
24) 4-(3-(2-(dimethylamino)ethoxy)-5-methoxyphenyl)-N-(3-methoxy-6-methylfuro[2,3-b]pyrazin-2-yl)piperazine-1-carboxamide,
25) 4-(3,5-dimethylphenyl)-N-(3-methoxy-6-methylfuro[2,3-b]pyrazin-2-yl)piperazine-1-carboxamide,
26) 4-(3-fluoro-5-methylphenyl)-N-(3-methoxy-6-methylfuro[2,3-b]pyrazin-2-yl)piperazine-1-carboxamide,
27) 4-(3,5-difluorophenyl)-N-(3-methoxy-6-methylfuro[2,3-b]pyrazin-2-yl)piperazine-1-carboxamide,
28) 4-(3-fluoro-5-(trifluoromethyl)phenyl)-N-(3-methoxy-6-methylfuro[2,3-b]pyrazin-2-yl)piperazine-1-carboxamide,
29) 4-(3,5-bis(trifluoromethyl)phenyl)-N-(3-methoxy-6-methylfuro[2,3-b]pyrazin-2-yl)piperazine-1-carboxamide,
30) N-(3-methoxy-6-methylfuro[2,3-b]pyrazin-2-yl)-4-(3-(trifluoromethoxy)phenyl)piperazine-1-carboxamide,
31) 4-(3,5-dimethoxyphenyl)-N-(3-ethoxy-6-methylfuro[2,3-b]pyrazin-2-yl)piperazine-1-carboxamide,
32) N-(3-ethoxy-6-methylfuro[2,3-b]pyrazin-2-yl)-4-(3-methoxy-5-methylphenyl)piperazine-1-carboxamide,
33) N-(3-ethoxy-6-methylfuro[2,3-b]pyrazin-2-yl)-4-(3-fluoro-5-methoxyphenyl)piperazine-1-carboxamide,
34) 4-(3-(2-(dimethylamino)ethoxy)-5-methoxyphenyl)-N-(3-ethoxy-6-methylfuro[2,3-b]pyrazin-2-yl)piperazine-1-carboxamide,
35) 4-(3,5-dimethylphenyl)-N-(3-ethoxy-6-methylfuro[2,3-b]pyrazin-2-yl)piperazine-1-carboxamide,
36) N-(3-ethoxy-6-methylfuro[2,3-b]pyrazin-2-yl)-4-(3-fluoro-5-methylphenyl)piperazine-1-carboxamide,
37) 4-(3,5-difluorophenyl)-N-(3-ethoxy-6-methylfuro[2,3-b]pyrazin-2-yl)piperazine-1-carboxamide,
38) N-(3-ethoxy-6-methylfuro[2,3-b]pyrazin-2-yl)-4-(3-fluoro-5-(trifluoromethyl)phenyl)piperazine-1-carboxamide, 39) 4-(3,5-bis(trifluoromethyl)phenyl)-N-(3-ethoxy-6-methylfuro[2,3-b]pyrazin-2-yl)piperazine-1-carboxamide,
40) N-(3-ethoxy-6-methylfuro[2,3-b]pyrazin-2-yl)-4-(3-(trifluoromethoxy)phenyl)piperazine-1-carboxamide,
41) N-(6-chloro-3-methoxyfuro[2,3-b]pyrazin-2-yl)-4-(3,5-dimethoxyphenyl)piperazine-1-carboxamide,
42) N-(6-chloro-3-methoxyfuro[2,3-b]pyrazin-2-yl)-4-(3-methoxy-5-methylphenyl)piperazine-1-carboxamide,
43) N-(6-chloro-3-methoxyfuro[2,3-b]pyrazin-2-yl)-4-(3-fluoro-5-methoxyphenyl)piperazine-1-carboxamide,
44) N-(6-chloro-3-methoxyfuro[2,3-b]pyrazin-2-yl)-4-(3-(2-(dimethylamino)ethoxy)-5-methoxyphenyl)piperazine-1-carboxamide,
45) N-(6-chloro-3-methoxyfuro[2,3-b]pyrazin-2-yl)-4-(3,5-dimethylphenyl)piperazine-1-carboxamide,
46) N-(6-chloro-3-methoxyfuro[2,3-b]pyrazin-2-yl)-4-(3-fluoro-5-methylphenyl)piperazine-1-carboxamide,
47) N-(6-chloro-3-methoxyfuro[2,3-b]pyrazin-2-yl)-4-(3,5-difluorophenyl)piperazine-1-carboxamide,
48) N-(6-chloro-3-methoxy-furo[2,3-b]pyrazin-2-yl)-4-(3-fluoro-5-(trifluoromethyl)phenyl)piperazine-1-carboxamide,
49) 4-(3,5-bis(trifluoromethyl)phenyl)-N-(6-chloro-3-methoxy-furo[2,3-b]pyrazin-2-yl)piperazine-1-carboxamide,
50) N-(6-chloro-3-methoxy-furo[2,3-b]pyrazin-2-yl)-4-(3-(trifluoromethoxy)phenyl)piperazine-1-carboxamide,
51) N-(6-chloro-3-ethoxyfuro[2,3-b]pyrazin-2-yl)-4-(3,5-dimethoxyphenyl)piperazine-1-carboxamide,
52) N-(6-chloro-3-ethoxyfuro[2,3-b]pyrazin-2-yl)-4-(3-methoxy-5-methylphenyl)piperazine-1-carboxamide,
53) N-(6-chloro-3-ethoxyfuro[2,3-b]pyrazin-2-yl)-4-(3-fluoro-5-methoxyphenyl)piperazine-1-carboxamide,
54) N-(6-chloro-3-ethoxyfuro[2,3-b]pyrazin-2-yl)-4-(3-(2-(dimethylamino)ethoxy)-5-methoxyphenyl) piperazine-1-carboxamide,
55) N-(6-chloro-3-ethoxyfuro[2,3-b]pyrazin-2-yl)-4-(3,5-dimethylphenyl)piperazine-1-carboxamide,
56) N-(6-chloro-3-ethoxyfuro[2,3-b]pyrazin-2-yl)-4-(3-fluoro-5-methylphenyl)piperazine-1-carboxamide,
57) N-(6-chloro-3-ethoxyfuro[2,3-b]pyrazin-2-yl)-4-(3,5-difluorophenyl)piperazine-1-carboxamide,
58) N-(6-chloro-3-ethoxyfuro[2,3-b]pyrazin-2-yl)-4-(3-fluoro-5-(trifluoromethyl)phenyl)piperazine-1-carboxamide,
59) 4-(3,5-bis(trifluoromethyl)phenyl)-N-(6-chloro-3-ethoxyfuro[2,3-b]pyrazin-2-yl)piperazine-1-carboxamide, or
60) N-(6-chloro-3-ethoxyfuro[2,3-b]pyrazin-2-yl)-4-(3-(trifluoromethoxy)phenyl)piperazine-1-carboxamide.

In the specific exemplary embodiments of the present invention, 60 compounds were synthesized, and the types of substituents of each compound are summarized in Tables 1 to 11.

The compound of the present invention can exist in the form of a salt, especially a pharmaceutically acceptable salt. For the salt, a salt commonly used in the art, such as an acid-addition salt formed by a pharmaceutically acceptable free acid, can be used without limitation. As used herein, the term "pharmaceutically acceptable salt" refers to any organic or inorganic addition salt having an effective active concentration that is relatively non-toxic and harmless to the patients and whose side effects do not degrade the beneficial efficacy of the compound represented by Formula 1.

An acid-addition salt can be prepared by a conventional method. For example, after dissolving the compound in an excess amount of an acid solution, the salt is produced from precipitation with a water-miscible organic solvent such as methanol, ethanol, acetone, or acetonitrile. In addition, a mixture of equimolar amounts of the compound and an acid or alcohol (e.g., glycol monomethylether) in water can be heated and subsequently dried by evaporation to produce a salt, or to result in a precipitated salt, which is further subject to suction filtration to produce a final salt.

For the free acid, an organic and inorganic acid may be used. For example, an inorganic acid such as hydrochloric acid, phosphoric acid, sulfuric acid, nitric acid, tartaric acid, etc., and an organic acid such as methanesulfonic acid, p-toluenesulfonic acid, acetic acid, trifluoroacetic acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc. may be used herein, but the free acid is not limited thereto.

Additionally, the pharmaceutically acceptable metal salt may be prepared using a base. An alkali metal or alkaline earth metal salt can be obtained, for example, by dissolving the compound in an excess amount of an alkali metal hydroxide or alkaline earth metal hydroxide solution, whereupon the insoluble salts in the compound are filtered and the remaining filtrate is subject to evaporation and drying. Herein, it is pharmaceutically suitable to prepare a sodium, potassium, or calcium salt as the metal salt, but the metal salt is not limited thereto. In addition, the corresponding silver salt can be obtained by reacting an alkali metal or alkaline earth metal salt with a suitable silver salt (e.g., silver nitrate).

The pharmaceutically acceptable salt of the compound of the present invention comprises a salt of an acidic or basic group that may be present in the compound of Formula 1, unless otherwise indicated. For example, the pharmaceutically acceptable salt includes sodium, calcium, and potassium salts of a hydroxy group, and other pharmaceutically acceptable salts of an amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate), p-toluenesulfonate (tosylate), etc. The salt may be prepared using a salt preparation method known in the art.

For the pharmaceutically acceptable salt of the compound represented by Formula 1 of the present invention, any salts may be used without limitation as long as they are salts of compounds which inhibit proliferation of cancer cells and show an effecting of inducing apoptosis equivalently to the compound represented by Formula 1.

Additionally, the compound represented by Formula 1 according to the present invention includes not only a pharmaceutically acceptable salt but also a solvate such as a hydrate that can possibly be prepared therefrom, without limitation. The solvate of the compound represented by Formula 1 can be prepared from the compound represented by Formula 1 using a method known in the art.

Additionally, the compound represented by Formula 1 according to the present invention can be prepared in a crystalline or non-crystalline form. Further, when the compound of Formula 1 is prepared in a crystalline form, it may be randomly hydrated or solvated. In the present invention, the compound represented by Formula 1 may not only include a stoichiometric hydrate, but may also include a compound containing various amounts of water. The solvate of the compound represented by Formula 1 according to the present invention includes both stoichiometric solvates and non-stoichiometric solvates.

In another aspect, the present invention provides a method for preparing a compound represented by the following Formula 1, comprising: a first step of preparing a compound represented by the following Formula 3 from a compound represented by the following Formula 2; and a second step of preparing the compound represented by the following Formula 1 by reacting the compound represented by the following Formula 3 with a compound represented by the following Formula 4:

ii) a step of substituting the chloro in the compound represented by Formula 6 with trimethylsilylethynyl or propyne to obtain a compound represented by the following Formula 7;

iii) a step of carrying out a cyclization reaction of the compound represented by Formula 7 to obtain a compound represented by the following Formula 8;

iv) a step of substituting the compound represented by Formula 8 with tert-butyl carbamate to obtain a compound represented by the following Formula 9;

v) a step of removing the tert-butyl carboxyl from the compound represented by Formula 9 to obtain a compound represented by the following Formula 10;

vi) a step of halogenating the compound represented by Formula 10 to obtain a compound represented by the following Formula 11; and vii) a step of selectively substituting the halogen on the pyrazine ring of the compound represented by Formula 11 with a $C_{1-6}$ alkoxy group, but the synthesis method is not limited thereto. As long as the compound represented by Formula 2 can be obtained as a product, any synthesis method known in the art can be carried out without any modification or with partial modifications.

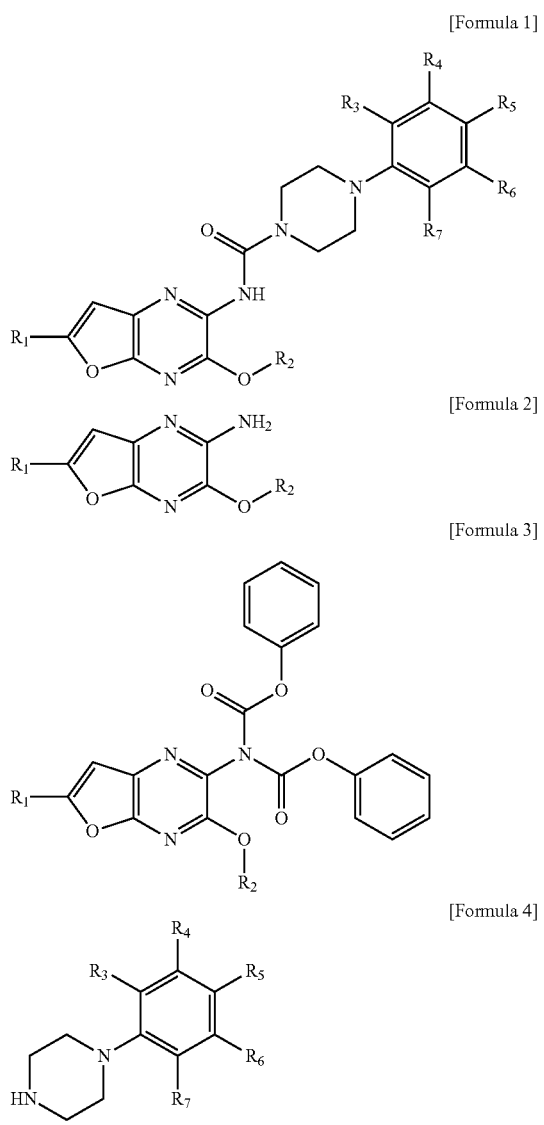

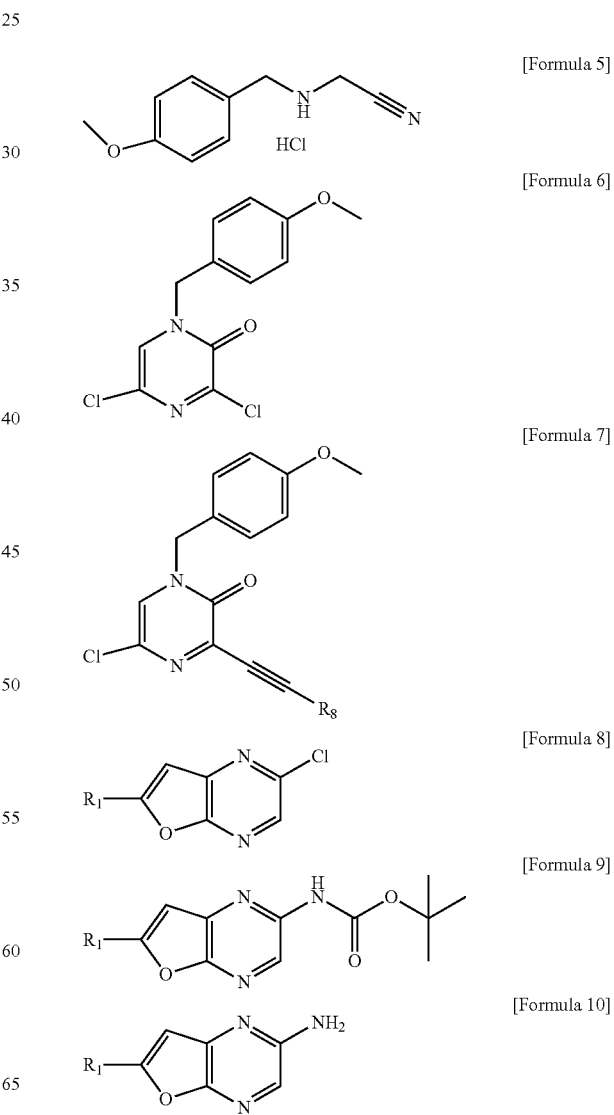

wherein $R_1$ to $R_7$ are as defined above.

Preferably, the compound represented by Formula 2 may be synthesized from 2-((4-methoxybenzyl)amino)acetonitrile or a salt thereof. The salt may be hydrochloride, but is not limited thereto.

More preferably, the compound represented by Formula 2 may be synthesized by:

i) a step of carrying out a cyclization reaction of a compound represented by the following Formula 5 to obtain a compound represented by the following Formula 6;

-continued

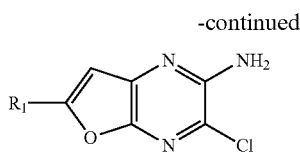

[Formula 11]

wherein $R_1$ may be defined as above; and $R_8$ may be trimethylsilyl or methyl.

For example, when the $R_8$ is trimethylsilyl, the step iii) further comprises a step of carrying out a cyclization reaction of the compound of Formula 7 to obtain a compound represented by the following Formula 12 as an intermediate:

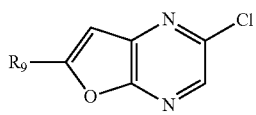

[Formula 12]

wherein $R_9$ may be trimethylsilyl.

In particular, step iii) may further comprise a step of removing or halogenating the trimethylsilyl of the compound represented by Formula 12 in order to provide the compound represented by Formula 8.

In the specific exemplary embodiments of the present invention, a 3-($C_{1-6}$ alkoxy)furo[2,3-b]pyrazin-2-amine derivative was synthesized from 2-((4-methoxybenzyl)amino)acetonitrile hydrochloride. Thereafter, a 4-(unsubstituted or substituted phenyl)-N-(3-($C_{1-6}$ alkoxy)furo[2,3-b]pyrazin-3-yl)-piperazine-1-carboxamide derivative, which is the title compound, was synthesized therefrom.

In another aspect, the present invention provides a pharmaceutical composition for preventing or treating cancer, comprising the compound represented by Formula 1 or a pharmaceutically acceptable salt thereof as an active ingredient.

As used herein, the term "prevention" refers to all actions of suppressing or delaying the occurrence, spread, and recurrence of cancer diseases by administration of the composition of the present invention. In addition, as used herein, the term "treatment" refers to all actions in which symptoms of the diseases are improved or advantageously altered by administration of the composition of the present invention.

The pharmaceutical composition of the present invention can prevent or treat cancer by suppressing proliferation of cancer cells and inducing apoptosis. Preferably, non-limiting examples of cancers that can be prevented or treated using the pharmaceutical composition of the present invention are colon cancer, breast cancer, pancreatic cancer, head and neck cancer, kidney cancer, lung cancer, colorectal adenocarcinoma, or other adenocarcinoma.

Preferably, the pharmaceutical composition according to the present invention may comprise, as active ingredients, the compound represented by Formula 1 or a pharmaceutically acceptable salt thereof by 0.1 wt % to 75 wt %, more preferably 1 wt % to 50 wt %, based on the total weight of the composition.

The composition of the present invention can be used in various forms such as oral dosage forms of powders, granules, tablets, capsules, suspensions, emulsions, syrups, aerosols and injections of a sterile injectable solution formulated by a conventional method to serve the purpose of each, and can be administered through various routes including oral administration or intravenous, intraperitoneal, subcutaneous, rectal, and topical administration. Examples of suitable carriers, excipients, or diluents which can be included in this composition may be lactose, dextrose, sucrose, sorbitol, mannitol, xylitol, erythritol, maltitol, starch, acacia rubber, alginate, gelatin, calcium phosphate, calcium silicate, cellulose, methyl cellulose, amorphous cellulose, polyvinyl pyrrolidone, water, methyl hydroxy benzoate, propyl hydroxy benzoate, talc, magnesium stearate, and mineral oil. The composition of the present invention may further comprise fillers, anti-coagulants, lubricants, humectants, fragrances, emulsifiers, preservatives, etc.

Solid formulation agents for oral administration include tablets, pills, powders, granules, and capsules, and such solid dosage forms are formulated by mixing the composition in the present invention with one or more excipients, such as starch, calcium carbonate, sucrose, lactose, gelatin, etc. In addition, lubricants such as magnesium stearate and talc can be used in addition to simple excipients.

Liquid formulation agents for oral administration can be illustrated as suspensions, solution for internal use, emulsions, syrups, etc., and can include various excipients such as humectants, sweeteners, fragrances, preservatives, etc., in addition to water and liquid paraffin, which are commonly used as diluents.

Formulation agents for parenteral administration include a sterile aqueous solution, nonaqueous solvent, suspending agent, emulsion, lyophilization agent, and suppository agent. The nonaqueous solvent and suspending agent may include propylene glycol, polyethylene glycol, vegetable oil such as olive oil, and injectable esters such as ethyl oleate, etc. As substrates for the suppository formulation, Witepsol, Macrogol, twin 61, cacao butter, laurin butter, or glycerogelatin may be used. Meanwhile, injections may include conventional additives such as solvents, isotonic agent, suspending agents, emulsifiers, stabilizers, preservatives, etc.

The composition of the present invention is administered in a pharmaceutically effective amount. As used herein, the term "pharmaceutically effective amount" refers to an amount sufficient to treat diseases at a reasonable benefit/risk ratio applicable to any medical treatment, and refers to an amount that does not cause side effects. In addition, the effective dosage level of the composition may be determined depending on factors including the health condition of patients, the types of the disease, the severity of the disease, the activity of the drug, the patient's sensitivity to the drug, the administration method, the administration time, the route of administration, excretion rate, the duration of treatment, drugs used concurrently or in combination with the composition, and other factors well known in the medical field. The composition of the present invention may be administered individually or in combination with other therapeutic agents, and may be administered sequentially or simultaneously with conventional therapeutic agents. The composition may be administered in a single- or multiple-dosage form. It is important to administer the composition in the minimum amount that can exhibit the maximum effect without causing side effects, in view of all of the above-described factors, and it can be easily determined by one of ordinary skill in the art.

Specifically, the effective amount of the compound in the composition of the present invention can vary depending on the patient's age, sex, and body weight, and 1 mg to 100 mg in general, or 5 mg to 60 mg preferably per 1 kg of the body weight can be administered every day, every other day, or 1 to 3 times a day. However, the amount may be decreased or increased depending on the route of administration, the severity of the disease, sex, body weight, age, etc., and thus does not in any way limit the scope of the present invention.

The present invention also provides a method for preventing or treating a cancer disease from a subject, comprising a step of administering the pharmaceutical composition to a subject in need thereof.

As used herein, the term "subject" refers to an animal including a human who has the cancer or is likely to have the cancer, a monkey, a cow, a horse, a sheep, a pig, a chicken, a turkey, a quail, a cat, a dog, a mouse, a rat, a rabbit, or a guinea pig, and the disease can be effectively prevented or treated by administering the pharmaceutical composition of the present invention to a subject. The pharmaceutical composition of the present invention can be administered concurrently with conventional therapeutic agents.

As used herein, the term "administration" refers to introduction of a predetermined material to a patient by any appropriate methods, and the administration route of the composition of the present invention can be administered by any general route as long as the composition reaches the target tissues. The pharmaceutical composition of the present invention may be administered through intraperitoneal administration, intravenous administration, intramuscular administration, subcutaneous administration, intradermal administration, oral administration, topical administration, intranasal administration, intrapulmonary administration, or intrarectal administration, but is not limited thereto. Additionally, the pharmaceutical composition of the present invention may also be administered by any device capable of transferring the active agent to the target cells. A preferable administration mode and formulation are an intravenous injection, a subcutaneous injection, an intradermal injection, an intramuscular injection, instillation, etc. Injectable formulations can be prepared using aqueous solvents, such as physiological saline, Ringer's solution, etc., or non-aqueous solvents, such as vegetable oils, higher fatty acid esters (e.g., ethyl oleate), alcohols (e.g., ethanol, benzyl alcohol, propylene glycol, glycerin, etc.). In addition, the composition may comprise pharmaceutically acceptable carriers, including a stabilizer for preventing degeneration (e.g., ascorbic acid, sodium bisulfite, sodium pyrosulfite, BHA, tocopherol, EDTA, etc.), an emulsifier, a buffering agent for pH control, and a preservative for inhibiting microbial growth (e.g., phenylmercuric nitrate, thimerosal, benzalkonium chloride, phenol, cresol, benzyl alcohol, etc.).

The term "therapeutically effective amount" used in combination with the active ingredient in the present invention refers to an amount of the compound represented by Formula 1, which is effective for preventing or treating the target disease, or the pharmaceutically acceptable salt thereof.

In addition to the compound represented by Formula 1 or the pharmaceutically acceptable salt thereof used as an active ingredient, the pharmaceutical composition of the present invention may further comprise known drugs used for the prevention or treatment of each known disease depending on the types of diseases to be prevented or treated. For example, when used for the prevention or treatment of cancer diseases, the composition may further comprise anticancer agents known in the art, in addition to a (tetrahydroquinoline-4-yl)malonate derivative compound or a pharmaceutically acceptable salt thereof used as an active ingredient. Further, the composition can be used in combination with other therapies known for treating these diseases. Other therapies include chemotherapy, radiation therapy, hormonal therapy, bone marrow transplantation, stem-cell replacement therapy, other biological therapy, and immunotherapy, but are not limited thereto.

Examples of the anti-cancer agent which can be included in the pharmaceutical composition in the present invention include mechlorethamine, chlorambucil, phenylalanine, mustard, ifosfamide, carmustine (BCNU), lomustine (CCNU), streptozotocin, busulfan, thiotepa, cisplatin, and carboplatin as DNA alkylating agents; dactinomycin (actinomycin D), doxorubicin (adriamycin), daunorubicin, idarubicin, mitoxantrone, plicamycin, mitomycin C and bleomycin as anti-cancer antibiotics; and vincristine, vinblastine, paclitaxel, docetaxel, etoposide, teniposide, topotecan, and iridotecan as plant alkaloids, but are not limited thereto.

Mode for Carrying Out the Invention

Hereinbelow, the present invention will be described in detail with accompanying exemplary embodiments. However, the exemplary embodiments disclosed herein are only for illustrative purposes and should not be construed as limiting the scope of the present invention.

The types of substituents of 60 compounds represented by Formula 1, which were synthesized in the specific exemplary embodiments of the present invention, are summarized in Tables 1 to 11 below, together with LC/MS data.

[Formula 1]

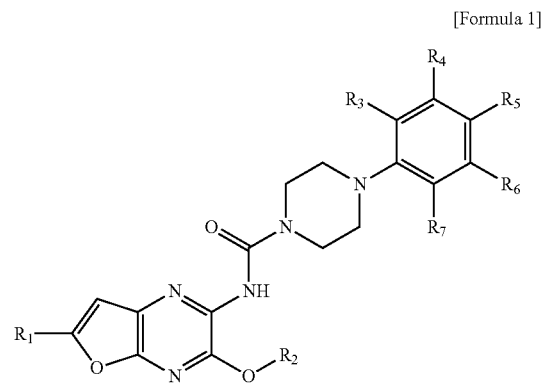

TABLE 1

| Example # | R1 | R2 | R3 | R4 | R5 | R6 | R7 | LC/MS(ESI) |
|---|---|---|---|---|---|---|---|---|
| 1 | H | methyl | H | methoxy | H | methoxy | H | 414 [M + H]+ |
| 2 | H | methyl | H | methoxy | H | methyl | H | 398 [M + H]+ |
| 3 | H | methyl | H | methoxy | H | fluoro | H | 402 [M + H]+ |
| 4 | H | methyl | H | methoxy | H | N,N-dimethyl aminoethoxy | H | 471 [M + H]+ |

TABLE 2

| | | | | | | | | |
|---|---|---|---|---|---|---|---|---|
| 5 | H | methyl | H | methyl | H | methyl | H | 382 [M + H]+ |
| 6 | H | methyl | H | methyl | H | fluoro | H | 386 [M + H]+ |
| 7 | H | methyl | H | fluoro | H | fluoro | H | 390 [M + H]+ |
| 8 | H | methyl | H | fluoro | H | trifluoro-methyl | H | 440 [M + H]+ |

TABLE 3

| 9  | H | methyl | H | trifluoromethyl | H | trifluoromethyl | H | 490 [M + H]⁺ |
|----|---|--------|---|-----------------|---|------------------|---|---------------|
| 10 | H | methyl | H | H               | H | trifluoromethoxy | H | 438 [M + H]⁺ |
| 11 | H | ethyl  | H | methoxy         | H | methoxy          | H | 428 [M + H]⁺+ |
| 12 | H | ethyl  | H | methoxy         | H | methyl           | H | 412 [M + H]⁺ |
| 13 | H | ethyl  | H | methoxy         | H | fluoro           | H | 416 [M + H]⁺ |
| 14 | H | ethyl  | H | methoxy         | H | N,N-dimethyl aminoethoxy | H | 485 [M + H]⁺ |

TABLE 4

| 15 | H | ethyl | H | methyl          | H | methyl          | H | 396 [M + H]⁺ |
|----|---|-------|---|-----------------|---|-----------------|---|---------------|
| 16 | H | ethyl | H | methyl          | H | fluoro          | H | 400 [M + H]⁺ |
| 17 | H | ethyl | H | fluoro          | H | fluoro          | H | 404 [M + H]⁺ |
| 18 | H | ethyl | H | fluoro          | H | trifluoromethyl | H | 454 [M + H]⁺ |
| 19 | H | ethyl | H | trifluoromethyl | H | trifluoromethyl | H | 504 [M + H]⁺ |

TABLE 5

| 20 | H      | ethyl  | H | H       | H | trifluoromethoxy         | H | 452[M + H]⁺ |
|----|--------|--------|---|---------|---|--------------------------|---|--------------|
| 21 | methyl | methyl | H | methoxy | H | methoxy                  | H | 428[M + H]⁺ |
| 22 | methyl | methyl | H | methoxy | H | methyl                   | H | 412[M + H]⁺ |
| 23 | methyl | methyl | H | methoxy | H | fluoro                   | H | 416[M + H]⁺ |
| 24 | methyl | methyl | H | methoxy | H | N,N-dimethyl aminoethoxy | H | 485[M + H]⁺ |
| 25 | methyl | methyl | H | methyl  | H | methyl                   | H | 396[M + H]⁺ |

TABLE 6

| 26 | methyl | methyl | H | methyl          | H | fluoro           | H | 400[M + H]⁺ |
|----|--------|--------|---|-----------------|---|------------------|---|--------------|
| 27 | methyl | methyl | H | fluoro          | H | fluoro           | H | 404[M + H]⁺ |
| 28 | methyl | methyl | H | fluoro          | H | trifluoromethyl  | H | 454[M + H]⁺ |
| 29 | methyl | methyl | H | trifluoromethyl | H | trifluoromethyl  | H | 504[M + H]⁺ |
| 30 | methyl | methyl | H | H               | H | trifluoromethoxy | H | 452[M + H]⁺ |
| 31 | methyl | ethyl  | H | methoxy         | H | methoxy          | H | 442[M + H]⁺ |

TABLE 7

| 32 | methyl | ethyl | H | methoxy | H | methyl                   | H | 426[M + H]⁺ |
|----|--------|-------|---|---------|---|--------------------------|---|--------------|
| 33 | methyl | ethyl | H | methoxy | H | fluoro                   | H | 430[M + H]⁺ |
| 34 | methyl | ethyl | H | methoxy | H | N,N-dimethyl aminoethoxy | H | 499[M + H]⁺ |
| 35 | methyl | ethyl | H | methyl  | H | methyl                   | H | 410[M + H]⁺ |
| 36 | methyl | ethyl | H | methyl  | H | fluoro                   | H | 414[M + H]⁺ |
| 37 | methyl | ethyl | H | fluoro  | H | fluoro                   | H | 418[M + H]⁺ |

TABLE 8

| 38 | methyl | ethyl  | H | fluoro          | H | trifluoromethyl  | H | 468[M + H]⁺ |
|----|--------|--------|---|-----------------|---|------------------|---|--------------|
| 39 | methyl | ethyl  | H | trifluoromethyl | H | trifluoromethyl  | H | 518[M + H]⁺ |
| 40 | methyl | ethyl  | H | H               | H | trifluoromethoxy | H | 466[M + H]⁺ |
| 41 | Cl     | methyl | H | methoxy         | H | methoxy          | H | 448[M + H]⁺ |
| 42 | Cl     | methyl | H | methoxy         | H | methyl           | H | 432[M + H]⁺ |

TABLE 9

| 43 | Cl | methyl | H | methoxy | H | fluoro       | H | 436[M + H]⁺ |
|----|----|--------|---|---------|---|--------------|---|--------------|
| 44 | Cl | methyl | H | methoxy | H | N,N-dimethyl | H | 505[M + H]⁺ |

TABLE 9-continued

| | | | | | | | | |
|---|---|---|---|---|---|---|---|---|
| 45 | Cl | methyl | H | methyl | H | aminoethoxy methyl | H | 416[M + H]+ |
| 46 | Cl | methyl | H | methyl | H | fluoro | H | 420[M + H]+ |
| 47 | Cl | methyl | H | fluoro | H | fluoro | H | 424[M + H]+ |
| 48 | Cl | methyl | H | fluoro | H | trifluoromethyl | H | 474[M + H]+ |

TABLE 10

| | | | | | | | | |
|---|---|---|---|---|---|---|---|---|
| 49 | Cl | methyl | H | trifluoromethyl | H | trifluoromethyl | H | 524[M + H]+ |
| 50 | Cl | methyl | H | H | H | trifluoromethoxy | H | 472[M + H]+ |
| 51 | Cl | ethyl | H | methoxy | H | methoxy | H | 462[M + H]+ |
| 52 | Cl | ethyl | H | methoxy | H | methyl | H | 446[M + H]+ |
| 53 | Cl | ethyl | H | methoxy | H | fluoro | H | 450[M + H]+ |
| 54 | Cl | ethyl | H | methoxy | H | N,N-dimethyl aminoethoxy | H | 519[M + H]+ |

TABLE 11

| | | | | | | | | |
|---|---|---|---|---|---|---|---|---|
| 55 | Cl | ethyl | H | methyl | H | methyl | H | 430[M + H]+ |
| 56 | Cl | ethyl | H | methyl | H | fluoro | H | 434[M + H]+ |
| 57 | Cl | ethyl | H | fluoro | H | fluoro | H | 438[M + H]+ |
| 58 | Cl | ethyl | H | fluoro | H | trifluoromethyl | H | 488[M + H]+ |
| 59 | Cl | ethyl | H | trifluoromethyl | H | trifluoromethyl | H | 538[M + H]+ |
| 60 | Cl | ethyl | H | H | H | trifluoromethoxy | H | 486[M + H]+ |

Example 1: 4-(3,5-Dimethoxyphenyl)-N-(3-methoxyfuro[2,3-b]pyrazin-2-yl)piperazine-1-carboxamide

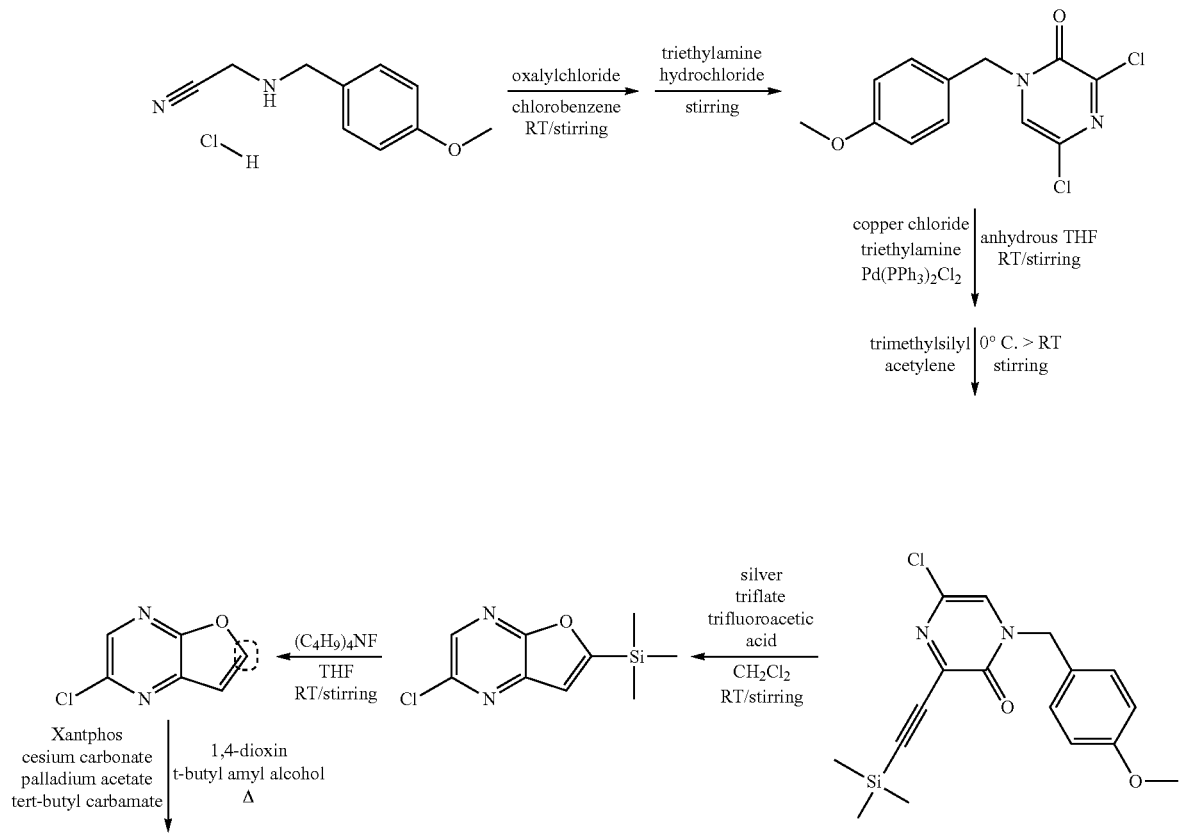

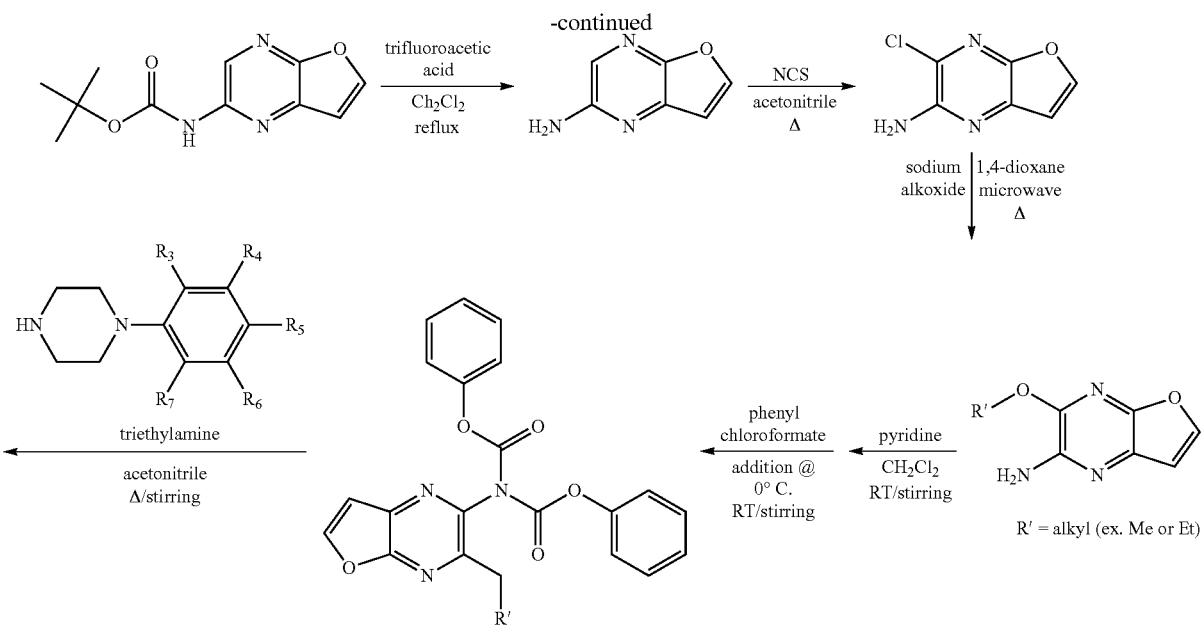

Step 1) Preparation of 3,5-dichloro-1-(4-methoxybenzyl)pyrazin-2(1H)-one

After dissolving 2-((4-methoxybenzyl)amino)acetonitrile hydrochloride (11.98 g, 56.50 mmol) in chlorobenzene (300 mL), oxalyl chloride (14.78 mL, 169.51 mmol) was slowly added under a nitrogen atmosphere. The reaction mixture was stirred at room temperature for 30 minutes, and then triethylamine triethylamine hydrochloride (38.88 g, 282.5 mmol) was added and stirred for 12 hours. The reaction mixture was filtered under reduced pressure, washed 3 times with dichloromethane, and then the filtrate was concentrated under reduced pressure. The residue was purified on a silica gel column by chromatography. A mixed solvent of hexane and ethyl acetate (2:1, v/v) was used for elution, and then the title compound (14.22 g, 89%) was obtained.

$^1$H NMR (500 MHz, CDCl$_3$) δ 7.31 (d, J=8.1 Hz, 2H), 7.18 (s, 1H), 6.94 (d, J=8.0 Hz, 2H), 5.06 (s, 2H), 3.84 (s, 3H).

Step 2) Preparation of 5-chloro-1-(4-methoxybenzyl)-3-((trimethylsilyl)ethynyl)pyrazin-2(1H)-one After dissolving 3,5-dichloro-1-(4-methoxybenzyl) pyrazin-2(1H)-one (20 g, 70.42 mmol) in anhydrous tetrahydrofuran (300 mL), copper chloride (1.34 g, 7.04 mmol), triethylamine (29.36 mL, 211.26 mmol), and bis(triphenylphosphine)palladium(II) dichloride (4.93 g, 7.04 mmol) were added under a nitrogen atmosphere and stirred at room temperature for 30 minutes. Trimethylsilyl acetylene (11.68 mL, 84.5 mmol) was slowly added dropwise to the reaction mixture at 0° C., and then the resultant was stirred at room temperature for 1 hour and filtered under reduced pressure using celite. The resultant was then washed about 3 times with ethyl acetate (50 mL) and was concentrated under reduced pressure. The residue was purified on a silica gel column by chromatography. A mixed solvent of hexane and ethyl acetate (4:1, v/v) was used for elution, and then the title compound (17 g, 70%) was obtained.

$^1$H NMR (500 MHz, CDCl$_3$) δ 7.25 (s, 1H), 7.26 (d, J=8.1 Hz, 2H), 6.84 (d, J=8.0 Hz, 2H), 4.98 (s, 2H), 3.76 (s, 3H), 0.24 (s, 9H).

Step 3) Preparation of 2-chloro-6-(trimethylsilyl) furo[2,3-b]pyrazine

After dissolving 5-chloro-1-(4-methoxybenzyl)-3-((trimethylsilyl)ethynyl)pyrazin-2(1H)-one (13.5 g, 39.01 mmol) in dichloromethane (300 mL), silver triflate (2.48 g, 9.67 mmol), and trifluoroacetic acid (14.93 mL, 195.00 mmol) were added and filtered at room temperature for 30 minutes. The reaction mixture was neutralized with a saturated aqueous sodium hydroxide solution at 0° C., extracted with dichloromethane, and then dried over anhydrous magnesium sulfate. The remaining residue was purified on a silica gel column by chromatography. A mixed solvent of hexane and ethyl acetate (5:1, v/v) was used for elution, and then the title compound (11.49 g, 85%) was obtained.

$^1$H NMR (500 MHz, CDCl$_3$) δ 8.47 (s, 1H), 8.30 (s, 1H), 0.37 (s, 9H).

Step 4) Preparation of 2-chlorofuro[2,3-b]pyrazine

After dissolving 2-chloro-6-(trimethylsilyl)furo[2,3-b] pyrazine (4.4 g, 19.46 mmol) in tetrahydrofuran (150 mL), 1 M tetrabutyl ammonium fluoride (29.19 mL, 29.19 mmol) was added and then stirred at room temperature for 30 minutes. The solvent was concentrated under reduced pressure, and the remaining residue was purified on a silica gel column by chromatography. A mixed solvent of hexane and ethyl acetate (5:1, v/v) was used for elution, and then the title compound (2.54 g, 85%) was obtained.

$^1$H NMR (500 MHz, CDCl$_3$) δ 8.29 (s, 1H), 8.04 (d, J=2.6 Hz, 1H), 7.00 (d, J=2.6 Hz, 1H).

Step 5) Preparation of tert-butyl furo[2,3-b]pyrazin-2-ylcarbamate

After dissolving 2-chlorofuro[2,3-b]pyrazine (2.54 g, 16.48 mmol) in a mixture solution of 1,4-dioxin and tertbutylamyl alcohol (10:1, v/v, 90 mL), 4,5-bis(diphenylphosphino)-9,9-dimethylxanthene (1.69 g, 2.92 mmol), cesium carbonate (10.74 g, 32.97 mmol), palladium acetate (0.37 g, 1.64 mmol), and tert-butyl carbamate (2.87 g, 24.56 mmol) were added and then heated at 90° C. for 5 hours. The reaction mixture was cooled to room temperature, filtered under reduced pressure using celite, and then the solvent was concentrated under reduced pressure. The remaining residue was purified on a silica gel column by chromatography. A mixed solvent of hexane and ethyl acetate (5:1, v/v) was used for elution, and then the title compound (2.91 g, 75%) was obtained.

$^1$H NMR (500 MHz, CDCl$_3$) δ 9.02 (s, 1H), 7.94 (d, J=2.5 Hz, 1H), 7.84 (s, 1H), 6.88 (d, J=2.5 Hz, 1H), 1.55 (s, 9H).

Step 6) Preparation of furo[2,3-b]pyrazin-2-amine

After dissolving tert-butyl furo[2,3-b]pyrazin-2-ylcarbamate (8.92 g, 37.97 mmol) in dichloromethane (250 mL), trifluoroacetic acid (29 mL, 379.7 mmol) was added and then refluxed for 1 hour. The reaction mixture was neutralized with a saturated aqueous sodium hydroxide solution at 0° C., extracted with dichloromethane, and then dried over anhydrous magnesium sulfate. The organic layer was concentrated under reduced pressure to obtain the title compound (4.71 g, 92%).

$^1$H NMR (500 MHz, CDCl$_3$) δ 7.83 (d, J=2.5 Hz, 1H), 7.68 (s, 1H), 6.76 (d, J=2.4 Hz, 1H), 4.65 (brs, 2H).

Step 7) Preparation of 3-chlorofuro[2,3-b]pyrazin-2-amine

After dissolving furo[2,3-b]pyrazin-2-amine (0.1 g, 0.74 mmol) in acetonitrile (10 mL), N-chlorosuccinimide (0.11 g, 0.81 mmol) was added and heated at 90° C. for 30 minutes. The reaction mixture was cooled to room temperature, extracted with ethyl acetate, and then dried over anhydrous magnesium sulfate. The organic layer was concentrated under reduced pressure and the remaining residue was purified on a silica gel column by chromatography. A mixed solvent of hexane and ethyl acetate (4:1, v/v) was used for elution, and then the title compound (0.52 g, 69%) was obtained.

$^1$H NMR (500 MHz, CDCl$_3$) δ 7.82 (d, J=2.4 Hz, 1H), 6.78 (d, J=2.5 Hz, 1H), 4.97 (brs, 2H).

Step 8) Preparation of 3-methoxyfuro[2,3-b]pyrazin-2-amine

After dissolving 3-chlorofuro[2,3-b]pyrazin-2-amine (0.45 g, 2.66 mmol) in 1,4-dioxane (10 mL), a sodium methoxide solution (30% in methanol, 0.99 mL, 5.32 mmol) was added and stirred using a microwave reactor at 100° C. for 30 minutes. The reaction mixture was cooled to room temperature, and then the solvent was concentrated under reduced pressure, followed by extraction with ethyl acetate and drying over anhydrous magnesium sulfate. The organic layer was concentrated under reduced pressure and the remaining residue was purified on a silica gel column by chromatography. A mixed solvent of hexane and ethyl acetate (3:1, v/v) was used for elution, and then the title compound (0.31 g, 70%) was obtained.

$^1$H NMR (500 MHz, CDCl$_3$) δ 7.59 (d, J=2.3 Hz, 1H), 6.72 (d, J=2.3 Hz, 1H), 4.78 (brs, 2H), 4.09 (s, 3H).

Step 9) Preparation of phenyl N-(3-methoxy-furo[2,3-b]pyrazin-2-yl)-N-phenoxycarbonylcarbamate After dissolving 3-methoxyfuro[2,3-b]pyrazin-2-amine (0.32 g, 1.94 mmol) in dichloromethane (20 mL), pyridine (2.18 mL, 27.14 mmol) was added and then stirred at room temperature for 30 minutes. The reaction mixture was cooled to 0° C., and phenyl chloroformate (1.09 mL, 8.72 mmol) was added and then stirred at room temperature for 5 hours. The reaction mixture was extracted with ethyl acetate and dried over anhydrous magnesium sulfate. The organic layer was concentrated under reduced pressure and the remaining residue was purified on a silica gel column by chromatography. A mixed solvent of hexane and ethyl acetate (4:1, v/v) was used for elution, and then the title compound (0.63 g, 80%) was obtained.

$^1$H NMR (500 MHz, CDCl$_3$) δ 7.72 (d, J=2.3 Hz, 1H), 7.54-7.45 (m, 4H), 7.37-7.41 (m, 3H), 7.23-7.35 (m, 4H), 7.08 (d, J=2.3 Hz, 1H), 4.09 (s, 31-1).

Step 10) Preparation of 4-(3,5-dimethoxyphenyl)-N-(3-methoxyfuro[2,3-b]pyrazin-2-yl)piperazine-1-carboxamide After dissolving phenyl N-(3-methoxy-furo[2,3-b]pyrazin-2-yl)-N-phenoxycarbonylcarbamate (0.097 g, 0.24 mmol) in acetonitrile (10 mL), 1-(3,5-dimethoxyphenyl)piperazine (0.16 g, 0.72 mmol) and triethylamine (0.1 mL, 0.72 mmol) were added and then stirred at 60° C. for 5 hours. The reaction mixture was cooled to room temperature, extracted with ethyl acetate, and then dried over anhydrous magnesium sulfate. The organic layer was concentrated under reduced pressure and the remaining residue was purified on a silica gel column by chromatography. A mixed solvent of hexane and ethyl acetate (1:1, v/v) was used for elution, and then the title compound (0.08 g, 80%) was obtained.

$^1$H NMR (500 MHz, CDCl$_3$) δ 7.70 (d, J=2.4 Hz, 1H), 7.00 (s, 1H), 6.92 (d, J=2.4 Hz, 114), 6.12 (d, J=1.9 Hz, 2H), 6.09 (d, J=1.9 Hz, 1H), 4.12 (s, 3H), 3.81 (s, 6H), 3.77-3.72 (m, 4H), 3.32-3.26 (m, 4H).

Example 2: 4-(3-Methoxy-5-methylphenyl)-N-(3-methoxyfuro[2,3-b]pyrazin-2-yl)piperazine-1-carboxamide The title compound (70.5 mg, 72%) was synthesized in the same manner as in Example 1, except that 1-(3-methoxy-5-methylphenyl)piperazine was used instead of 1-(3,5-dimethoxyphenyl)piperazine in Step 10 of Example 1.

$^1$H NMR (500 MHz, CDCl$_3$) δ 7.70 (d, J=1.7 Hz, 1H), 7.00 (s, 1H), 6.92 (d, J=1.7 Hz, 1H), 6.41 (s, 1H), 6.32 (s, 2H), 4.12 (s, 3H), 3.81 (s, 3H), 3.77-3.71 (m, 4H), 3.32-3.24 (m, 4H), 2.33 (s, 3H).

Example 3: 4-(3-Fluoro-5-methoxyphenyl)-N-(3-methoxyfuro[2,3-b]pyrazin-2-yl)piperazine-1-carboxamide The title compound (140 mg, 74%) was synthesized in the same manner as in Example 1, except that 1-(3-fluoro-5-methoxyphenyl)piperazine was used instead of 1-(3,5-dimethoxyphenyl)piperazine in Step 10 of Example 1.

$^1$H NMR (500 MHz, CDCl$_3$) δ 7.68 (d, J=2.5 Hz, 1H), 6.99 (s, 1H), 6.90 (d, J=2.6 Hz, 1H), 6.21-6.48 (m, 3H), 4.10 (s, 3H), 3.78 (s, 3H), 3.68-3.72 (m, 4H), 3.28-3.40 (m, 4H).

Example 4: 4-(3-(2-(Dimethylamino)ethoxy)-5-methoxyphenyl)-N-(3-methoxyfuro[2,3-b]pyrazin-2-yl)piperazine-1-carboxamide The title compound (164 mg, 71%) was synthesized in the same manner as in Example 1, except that 2-(3-methoxy-5-

(piperazin-1-yl)phenoxy)-N,N-dimethylethan-1-amine was used instead of 1-(3,5-dimethoxyphenyl)piperazine in Step 10 of Example 1.

$^1$H NMR (500 MHz, CDCl$_3$) δ 7.78 (d, J=2.4 Hz, 1H), 7.00 (s, 1H), 6.95 (d, J=2.4 Hz, 1H), 6.12 (d, J=1.9 Hz, 2H), 6.08 (d, J=1.9 Hz, 1H), 4.69 (t, J=5.6 Hz, 2H), 4.12 (s, 3H), 3.81 (s, 3H), 3.77-3.72 (m, 4H), 3.32-3.26 (m, 4H), 2.80-3.10 (m, 2H), 2.46 (s, 6H).

Example 5: 4-(3,5-Dimethylphenyl)-N-(3-methoxy-furo[2,3-b]pyrazin-2-yl)piperazine-1-carboxamide The title compound (82 mg, 87%) was synthesized in the same manner as in Example 1, except that 1-(3,5-dimethylphenyl)piperazine was used instead of 1-(3,5-dimethoxyphenyl)piperazine in Step 10 of Example 1.

$^1$H NMR (500 MHz, CDCl$_3$) δ 7.70 (s, 1H), 7.03 (s, 1H), 6.92 (s, 1H), 6.50-6.60 (m, 3H), 4.12 (s, 3H), 3.62-3.75 (m, 4H), 3.18-3.25 (m, 4H), 2.32 (s, 6H).

Example 6: 4-(3-Fluoro-5-methylphenyl)-N-(3-methoxyfuro[2,3-b]pyrazin-2-yl)piperazine-1-carboxamide The title compound (130 mg, 70%) was synthesized in the same manner as in Example 1, except that 1-(3-fluoro-5-methylphenyl)piperazine was used instead of 1-(3,5-dimethoxyphenyl)piperazine in Step 10 of Example 1.

$^1$H NMR (500 MHz, CDCl$_3$) δ 7.68 (d, J=2.4 Hz, 1H), 7.10-6.96 (m, 1H), 6.90 (s, 1H), 6.51 (s, 1H), 6.42 (d, J=10.1 Hz, 2H), 4.10 (s, 3H), 3.68-3.72 (m, 4H), 3.20-3.29 (m, 4H), 2.31 (s, 3H).

Example 7: 4-(3,5-Difluorophenyl)-N-(3-methoxy-furo[23-b]pyrazin-2-yl)piperazine-1-carboxamide The title compound (72 mg, 75%) was synthesized in the same manner as in Example 1, except that 1-(3,5-difluorophenyl)piperazine was used instead of 1-(3,5-dimethoxyphenyl)piperazine in Step 10 of Example 1.

$^1$H NMR (500 MHz, CDCl$_3$) δ 7.70 (t, J=3.1 Hz, 1H), 7.01 (s, 1H), 6.91 (d, J=2.5 Hz, 1H), 6.44-6.36 (m, 2H), 6.33 (tt, J=8.8 Hz, 2.1 Hz, 1H), 4.12 (s, 3H), 3.78-3.73 (m, 4H), 3.35-3.29 (m, 4H).

Example 8: 4-(3-Fluoro-5-(trifluoromethyl)phenyl)-N-(3-methoxyfuro[2,3-b]pyrazin-2-yl)piperazine-1-carboxamide The title compound (72 mg, 75%) was synthesized in the same manner as in Example 1, except that 1-(3-fluoro-5-(trifluoromethyl)phenyl)piperazine was used instead of 1-(3,5-dimethoxyphenyl)piperazine in Step 10 of Example 1.

$^1$H NMR (500 MHz, CDCl$_3$) δ 7.69 (d, J=2.4 Hz, 1H), 7.14 (s, 1H), 6.90 (s, 1H), 6.88 (d, J=2.4 Hz, 1H), 6.80 (d, J=8.1 Hz, 1H), 6.71 (t, J=9.9 Hz, 1H), 4.08 (s, 3H), 3.78-3.73 (m, 4H), 3.39-3.28 (m, 4H).

Example 9: 4-(3,5-Bis(trifluoromethyl)phenyl)-N-(3-methoxyfuro[2,3-b]pyrazin-2-yl)piperazine-1-carboxamide The title compound (120 mg, 100%) was synthesized in the same manner as in Example 1, except that 1-(3,5-bis(trifluoromethyl)phenyl)piperazine was used instead of 1-(3,5-dimethoxyphenyl)piperazine in Step 10 of Example 1.

$^1$H NMR (500 MHz, CDCl$_3$) δ 7.71 (d, J=2.4 Hz, 1H), 7.36 (s, 1H), 7.28 (d, J=3.2 Hz, 1H), 7.04 (s, 1H), 6.91 (d, J=2.4 Hz, 1H), 4.12 (s, 3H), 3.84-3.76 (m, 4H), 3.45-3.36 (m, 4H).

Example 10: N-(3-Methoxyfuro[2,3-b]pyrazin-2-yl)-4-(3-(trifluoromethoxy)phenyl)piperazine-1-carboxamide The title compound (81 mg, 75%) was synthesized in the same manner as in Example 1, except that 1-(3-(trifluoromethyl)phenyl)piperazine was used instead of 1-(3,5-dimethoxyphenyl)piperazine in Step 10 of Example 1.

$^1$H NMR (500 MHz, CDCl$_3$) δ 7.70 (s, 1H), 7.33-7.27 (m, 1H), 7.03 (s, 1H), 6.92 (s, 1H), 6.86 (d, J=8.2 Hz, 1H), 6.76 (d, J=9.0 Hz, 2H), 4.11 (s, 3H), 3.80-3.73 (m, 4H), 3.28-3.38 (m, 4H).

Example 11: 4-(3,5-Dimethoxyphenyl)-N-(3-ethoxyfuro[2,3-b]pyrazin-2-yl)piperazine-1-carboxamide The title compound (83 mg, 81%) was obtained by reacting phenyl N-(3-ethoxy-furo[2,3-b]pyrazin-2-yl)-N-phenoxycarbonylcarbamate, which is obtained by using sodium ethoxide instead of sodium methoxide in Step 8 of Example 1, with 1-(3,5-dimethoxyphenyl)piperazine in the same manner as in Step 10 of Example 1.

$^1$H NMR (500 MHz, CDCl$_3$) δ 7.66 (d, J=2.4 Hz, 1H), 7.03 (s, 1H), 6.88 (d, J=2.4 Hz, 1H), 6.02-6.18 (m, 3H), 4.52 (q, J=7.1 Hz, 2H), 3.79 (s, 6H), 3.75-3.70 (m, 4H), 3.32-3.14 (m, 4H), 1.47 (t, J=7.1 Hz, 3H).

Example 12: N-(3-Ethoxyfuro[2,3-b]pyrazin-2-yl)-4-(3-methoxy-5-methylphenyl)piperazine-1-carboxamide The title compound (83 mg, 81%) was obtained by reacting phenyl N-(3-ethoxy-furo[2,3-b]pyrazin-2-yl)-N-phenoxycarbonylcarbamate with 1-(3-methoxy-5-methylphenyl)piperazine in the same manner as in Step 10 of Example 1.

$^1$H NMR (500 MHz, CDCl$_3$) δ 7.68 (d, J=2.3 Hz, 1H), 7.05 (s, 1H), 6.90 (d, J=2.3 Hz, 1H), 6.40 (s, 1H), 6.32 (s, 2H), 4.53 (q, J=7.0 Hz, 2H), 3.80 (s, 3H), 3.72 (dd, J=27.2 Hz, 22.2 Hz, 4H), 3.39-2.95 (m, 4H), 2.33 (s, 3H), 1.49 (t, J=7.1 Hz, 3H).

Example 13: N-(3-Ethoxyfuro[2,3-b]pyrazin-2-yl)-4-(3-fluoro-5-methoxyphenyl)piperazine-1-carboxamide The title compound (83 mg, 84%) was obtained by reacting phenyl N-(3-ethoxy-furo[2,3-b]pyrazin-2-yl)-N-phenoxycarbonylcarbamate with 1-(3-fluoro-5-methoxyphenyl)piperazine in the same manner as in Step 10 of Example 1.

$^1$H NMR (500 MHz, CDCl$_3$) δ 7.67 (s, 1H), 7.07 (s, 1H), 6.89 (s, 1H), 6.21 (dd, J=31.8 Hz, 12.0 Hz, 3H), 4.52 (q, J=7.0 Hz, 2H), 3.78 (s, 3H), 3.75-3.70 (m, 4H), 3.36-3.21 (m, 4H), 1.48 (t, J=7.0 Hz, 3H).

Example 14: 4-(3-(2-(Dimethylamino)ethoxy)-5-methoxyphenyl)-N-(3-ethoxyfuro[2,3-b]pyrazin-2-yl)piperazine-1-carboxamide The title compound (77 mg, 69%) was obtained by reacting phenyl N-(3-ethoxy-furo[2,3-b]pyrazin-2-yl)-N- phenoxycarbonylcarbamate with 2-(3-methoxy-5-(piperazine-1-yl)phenoxy)-N,N-dimethylethan-1-amine in the same manner as in Step 10 of Example 1.

$^1$H NMR (500 MHz, CDCl$_3$) δ 7.65 (d, J=2.3 Hz, 1H), 7.03 (s, 1H), 6.87 (d, J=2.4 Hz, 1H), 6.02-6.20 (m, 3H), 4.69 (t, J=5.6 Hz, 2H), 4.53 (q, J=7.1 Hz, 2H), 3.79 (s, 3H), 3.75-3.70 (m, 4H), 3.32-3.14 (m, 4H), 2.80-3.10 (m, 2H), 2.46 (s, 6H), 1.47 (t, J=7.1 Hz, 3H).

Example 15: 4-(3,5-Dimethylphenyl)-N-(3-ethoxy-furo[2,3-b]pyrazin-2-yl)piperazine-1-carboxamide The title compound (70 mg, 74%) was obtained by reacting phenyl N-(3-ethoxy-furo[2,3-b]pyrazin-2-yl)-N-phenoxycarbonylcarbamate with 1-(3,5-dimethylphenyl)piperazine in the same manner as in Step 10 of Example 1.

$^1$H NMR (500 MHz, CDCl$_3$) δ 7.67 (d, J=2.6 Hz, 1H), 7.09 (s, 1H), 6.90 (d, J=2.5 Hz, 1H), 6.55-6.70 (m, 3H), 4.54 (q, J=6.9 Hz, 2H), 3.84-3.52 (m, 4H), 3.34-3.09 (m, 4H), 2.44 (s, 6H), 1.49 (t, J=7.0 Hz, 2H).

Example 16: N-(3-Ethoxyfuro[2,3-b]pyrazin-2-yl)-4-(3-fluoro-5-methylphenyl)piperazine-1-carboxamide The title compound (61.8 mg, 65%) was obtained by reacting phenyl N-(3-ethoxy-furo[2,3-b]pyrazin-2-yl)-N-phenoxycarbonylcarbamate with 1-(3-fluoro-5-methylphenyl)piperazine in the same manner as in Step 10 of Example 1.

$^1$H NMR (500 MHz, CDCl$_3$) δ 7.68 (d, J=2.3 Hz, 1H), 7.07 (s, 1H), 6.90 (d, J=2.3 Hz, 1H), 6.52 (s, 1H), 6.43 (d, J=9.9 Hz, 2H), 4.53 (q, J=7.1 Hz, 2H), 3.79-3.71 (m, 4H), 3.32-3.22 (m, 4H), 2.32 (s, 3H), 1.49 (t, J=7.1 Hz, 3H).

Example 17: 4-(3,5-Difluorophenyl)-N-(3-ethoxy-furo[2,3-b]pyrazin-2-yl)piperazine-1-carboxamide The title compound (75 mg, 78%) was obtained by reacting phenyl N-(3-ethoxy-furo[2,3-b]pyrazin-2-yl)-N-phenoxycarbonylcarbamate with 1-(3,5-difluorophenyl)piperazine in the same manner as in Step 10 of Example 1.

$^1$H NMR (500 MHz, CDCl$_3$) δ 7.67 (d, J=2.4 Hz, 1H), 7.07 (s, 1H), 6.88 (d, J=2.4 Hz, 1H), 6.37 (d, J=8.5 Hz, 2H), 6.30 (dd, J=12.3 Hz, 5.4 Hz, 1H), 4.52 (q, J=7.1 Hz, 2H), 3.79-3.66 (m, 4H), 3.35-3.20 (m, 4H), 1.47 (t, J=7.1 Hz, 31-1).

Example 18: N-(3-Ethoxyfuro[2,3-b]pyrazin-2-yl)-4-(3-fluoro-5-(trifluoromethyl)phenyl)piperazine-1-carboxamide The title compound (73 mg, 70%) was obtained by reacting phenyl N-(3-ethoxy-furo[2,3-b]pyrazin-2-yl)-N-phenoxycarbonylcarbamate with 1-(3-fluoro-5-(trifluoromethyl)phenyl)piperazine in the same manner as in Step 10 of Example 1.

$^1$H NMR (500 MHz, CDCl$_3$) δ 7.65 (d, J=2.3 Hz, 1H), 7.06 (s, 1H), 6.90 (d, J=2.4 Hz, 1H), 6.39 (d, J=8.5 Hz, 2H), 6.35 (dd, J=12.3 Hz, 5.4 Hz, 1H), 4.51 (q, J=7.3 Hz, 2H), 3.75-3.66 (m, 4H), 3.35-3.24 (m, 4H), 1.47 (t, J=7.1 Hz, 3H).

Example 19: 4-(3,5-Bis(trifluoromethyl)phenyl)-N-(3-ethoxyfuro[2,3-b]pyrazin-2-yl)piperazine-1-carboxamide The title compound (78 mg, 67%) was obtained by reacting phenyl N-(3-ethoxy-furo[2,3-b]pyrazin-2-yl)-N-phenoxycarbonylcarbamate with 1-(3,5-bis(trifluoromethyl)phenyl)piperazine in the same manner as in Step 10 of Example 1.

$^1$H NMR (500 MHz, CDCl$_3$) δ 7.71 (d, J=2.3 Hz, 1H), 7.06 (s, 1H), 6.92 (d, J=2.4 Hz, 1H), 6.37 (d, J=8.5 Hz, 2H), 6.30 (dd, J=12.3 Hz, 5.4 Hz, 1H), 4.51 (q, J=7.3 Hz, 2H), 3.75-3.66 (m, 4H), 3.35-3.24 (m, 4H), 1.47 (t, J=7.1 Hz, 3H).

Example 20: N-(3-Ethoxyfuro[2,3-b]pyrazin-2-yl)-4-(3-(trifluoromethoxy)phenyl)piperazine-1-carboxamide The title compound (80 mg, 77%) was obtained by reacting phenyl N-(3-ethoxy-furo[2,3-b]pyrazin-2-yl)-N-phenoxycarbonylcarbamate with 1-(3-(trifluoromethoxy)phenyl)piperazine in the same manner as in Step 10 of Example 1.

$^1$H NMR (500 MHz, CDCl$_3$) δ 7.72 (s, 1H), 7.33-7.28 (m, 1H), 7.03 (s, 1H), 6.93 (s, 1H), 6.86 (d, J=8.2 Hz, 1H), 6.75 (d, J=9.0 Hz, 2H), 4.51 (q, J=7.3 Hz, 2H), 3.80-3.73 (m, 4H), 3.28-3.38 (m, 4H), 1.47 (t, J=7.1 Hz, 3H).

Example 21: 4-(3,5-Dimethoxyphenyl)-N-(3-methoxy-6-methylfuro[2,3-b]pyrazin-2-yl)piperazine-1-carboxamide

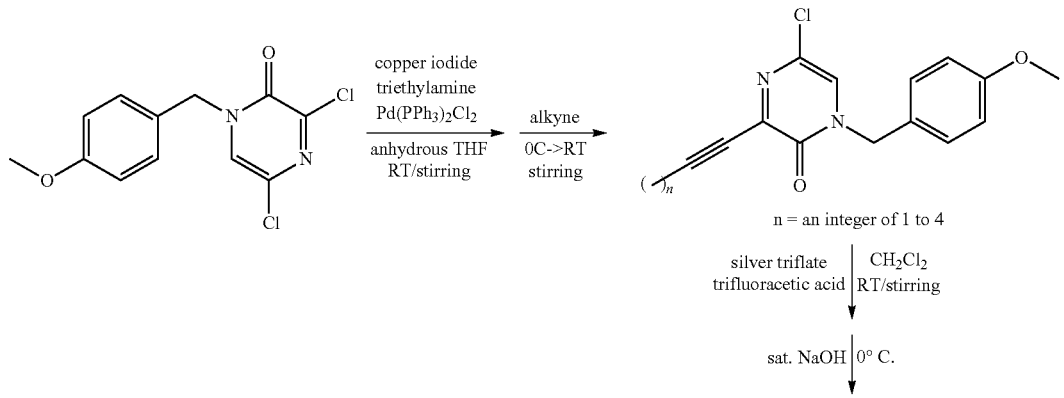

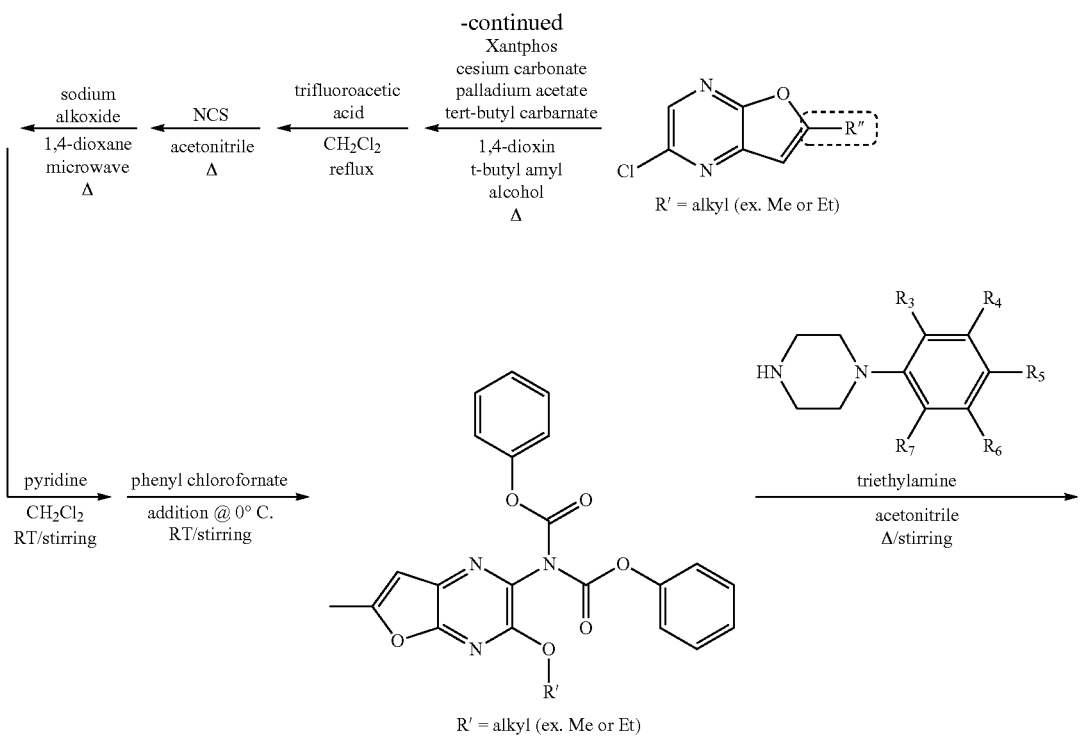

Step 1) Preparation of 5-chloro-1-(4-methoxybenzyl)-3-(propyn-1-yl)pyrazine-2(1H)-one After dissolving 3,5-dichloro-1-(4-methoxybenzyl)pyrazine-2(1H)-one (15 g, 52.81 mmol) in anhydrous tetrahydrofuran (350 mL), copper iodide (1 g, 5.28 mmol), triethylamine (22 mL, 158.43 mmol), and bis(triphenylphosphine)palladium(II) dichloride (3.70 g, 5.28 mmol) were added under a nitrogen atmosphere and stirred at room temperature for 30 minutes. Propyne (63.37 mL, 63.37 mmol, 4% in N,N-dimethylformamide) was slowly added dropwise to the reaction mixture at 0° C., stirred at room temperature for 6 hours, and then filtered under reduced pressure using celite. After washing about 3 times with ethyl acetate (50 mL), the filtrate was concentrated under reduced pressure, and the residue was purified on a silica gel column by chromatography. A mixed solvent of hexane and ethyl acetate (3:1, v/v) was used for elution, and then the title compound (10.64 g, 70%) was obtained.

$^1$H NMR (500 MHz, CDCl$_3$) δ 7.31 (d, J=8.6 Hz, 2H), 7.15 (s, 1H), 6.93 (d, J=8.7 Hz, 2H), 5.02 (s, 2H), 3.83 (s, 3H), 2.20 (s, 3H).

Step 2) Preparation of 2-chloro-6-methylfuro[2,3-b]pyrazine

After dissolving 5-chloro-1-(4-methoxybenzyl)-3-(propyn-1-yl)pyrazine-2(1H)-one (10.64 g, 36.96 mmol) in dichloromethane (250 mL), silver triflate (2.3 g, 9.16 mmol) and trifluoroacetic acid (14 mL, 184.83 mmol) were added and stirred at room temperature for 30 minutes. The reaction mixture was neutralized with a saturated aqueous sodium hydroxide solution at 0° C., extracted with dichloromethane, and then dried over anhydrous magnesium sulfate. The remaining residue was purified on a silica gel column by chromatography. A mixed solvent of hexane and ethyl acetate (4:1, v/v) was used for elution, and then the title compound (5.97 g, 96%) was obtained.

$^1$H NMR (500 MHz, CDCl$_3$) δ 8.17 (s, 1H), 6.63 (s, 1H), 2.61 (s, 3H).

Step 3) Preparation of tert-butyl (6-methylfuro[2,3-b]pyrazin-2-yl)carbamate The above compound (6.52 g, 74%) was obtained by carrying out the reaction in the same manner as in Step 5 of Example 1 using 2-chloro-6-methylfuro[2,3-b]pyrazine.

$^1$H NMR (500 MHz, CDCl$_3$) δ 8.86 (s, 1H), 7.28 (brs, 1H), 6.49 (d, J=0.9 Hz, 1H), 2.56 (s, 3H), 1.56 (s, 9H).

Step 4) Preparation of 6-methylfuro[2,3-b]pyrazin-2-amine

The above compound (3.26 g, 84%) was obtained by carrying out the reaction in the same manner as in Step 6 of Example 1 using tert-butyl (6-methylfuro[2,3-b]pyrazin-2-yl)carbamate.

$^1$H NMR (500 MHz, CDCl$_3$) δ 7.55 (s, 1H), 6.38 (d, J=0.9 Hz, 1H), 4.42 (brs, 2H), 2.51 (s, 3H).

Step 5) Preparation of 3-chloro-6-methylfuro[2,3-b]pyrazin-2-amine

The above compound (2.48 g, 62%) was obtained by carrying the reaction in the same manner as in Step 7 of Example 1 using 6-methylfuro[2,3-b]pyrazine-2-amine.

$^1$H NMR (500 MHz, CDCl$_3$) δ 6.40 (s, 1H), 4.91 (brs, 2H), 2.52 (s, 3H).

Step 6) Preparation of 3-methoxy-6-methylfuro[2,3-b]pyrazin-2-amine

The above compound (0.48 g, 70%) was obtained by carrying out the reaction in the same manner as in Step 8 of Example 1 using 3-chloro-6-methylfuro[2,3-b]pyrazine-2-amine.

¹H NMR (500 MHz, CDCl₃) δ 6.33 (s, 1H), 4.70 (brs, 2H), 4.04 (s, 3H), 2.45 (s, 3H).

Step 7) Preparation of phenyl N-(3-methoxy-6-methyl-furo[2,3-b]pyrazin-2-yl)-N-phenoxycarbonylcarbamate The above compound (0.67 g, 64%) was obtained by carrying out the reaction in the same manner as in Step 9 of Example 1 using 3-methoxy-6-methylfuro[2,3-b]pyrazine-2-amine.

¹H NMR (500 MHz, CDCl₃) δ 7.38 (t, J=7.8 Hz, 4H), 7.26 (dd, J=15.2 Hz, 8.0 Hz, 3H), 7.16 (d, J=8.3 Hz, 4H), 6.63 (s, 1H), 4.18 (s, 3H), 2.56 (s, 3H).

Step 8) Preparation of 4-(3,5-dimethoxyphenyl)-N-(3-methoxy-6-methylfuro[2,3-b]pyrazin-2-yl)piperazine-1-carboxamide The above compound (74 mg, 72%) was obtained by carrying out the reaction in the same manner as in Step 10 of Example 1 using phenyl N-(3-methoxy-6-methyl-furo[2,3-b]pyrazin-2-yl)-N-phenoxycarbonylcarbamate and 1-(3,5-dimethoxyphenyl)piperazine.

¹H NMR (500 MHz, CDCl₃) δ 6.93 (s, 1H), 6.51 (d, J=0.9 Hz, 1H), 6.09 (t, J=5.9 Hz, 2H), 6.06 (t, J=2.0 Hz, 1H), 4.06 (s, 3H), 3.79 (s, 6H), 3.72 (dd, J=11.2 Hz, 6.2 Hz, 4H), 3.28-3.17 (m, 4H), 2.48 (d, J=0.5 Hz, 3H).

Example 22: 4-(3-Methoxy-5-methylphenyl)-N-(3-methoxy-6-methylfuro[2,3-b]pyrazin-2-yl)piperazine-1-carboxamide The above compound (97 mg, 100%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3-methoxy-5-methylphenyl)piperazine.

¹H NMR (500 MHz, CDCl₃) δ 7.07 (s, 1H), 6.49 (s, 1H), 6.37 (s, 1H), 6.29 (s, 2H), 4.03 (s, 3H), 3.78 (s, 3H), 3.67-3.72 (m, 4H), 3.18-3.28 (m, 4H), 2.45 (s, 3H), 2.30 (s, 3H).

Example 23: 4-(3-Fluoro-5-methoxyphenyl)-N-(3-methoxy-6-methylfuro[2,3-b]pyrazin-2-yl)piperazine-1-carboxamide The above compound (95 mg, 96%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3-fluoro-5-methoxyphenyl)piperazine.

¹H NMR (500 MHz, CDCl₃) δ 6.91 (s, 1H), 6.51 (s, 1H), 6.29-6.12 (m, 3H), 4.06 (s, 3H), 3.78 (s, 3H), 3.75-3.65 (m, 4H), 3.32-3.22 (m, 4H), 2.48 (s, 3H).

Example 24: 4-(3-(2-(Dimethylamino)ethoxy)-5-methoxyphenyl)-N-(3-methoxy-6-methylfuro[2,3-b]pyrazin-2-yl)piperazine-1-carboxamide The above compound (84 mg, 73%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 2-(3-methoxy-5-(piperazine-1-yl)phenoxy)-N,N-dimethylethan-1-amine.

¹H NMR (500 MHz, CDCl₃) δ 6.91 (s, 1H), 6.51 (s, 1H), 6.29-6.12 (m, 3H), 4.69 (t, J=5.6 Hz, 2H), 4.06 (s, 3H), 3.78 (s, 3H), 3.75-3.65 (m, 4H), 3.32-3.22 (m, 4H), 2.80-3.10 (m, 2H), 2.49 (s, 3H), 2.46 (s, 6H).

Example 25: 4-(3,5-Dimethylphenyl)-N-(3-methoxy-6-methylfuro[2,3-b]pyrazin-2-yl)piperazine-1-carboxamide The above compound (81 mg, 87%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3,5-dimethylphenyl)piperazine.

¹H NMR (500 MHz, CDCl₃) δ 6.91 (s, 1H), 6.58 (s, 3H), 6.51 (s, 1H), 4.06 (s, 3H), 3.78-3.64 (m, 4H), 3.29-3.15 (m, 4H), 2.48 (s, 3H), 2.29 (s, 6H).

Example 26: 4-(3-Fluoro-5-methylphenyl)-N-(3-methoxy-6-methylfuro[2,3-b]pyrazin-2-yl)piperazine-1-carboxamide The above compound (75 mg, 79%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3-fluoro-5-methylphenyl)piperazine.

¹H NMR (500 MHz, CDCl₃) δ 6.94 (s, 1H), 6.51 (s, 2H), 6.42 (d, J=10.1 Hz, 2H), 4.06 (s, 3H), 3.72 (dd, J=11.3 Hz, 6.4 Hz, 4H), 3.31-3.15 (m, 4H), 2.48 (s, 3H), 2.31 (s, 3H).

Example 27: 4-(3,5-Difluorophenyl)-N-(3-methoxy-6-methylfuro[2,3-b]pyrazin-2-yl)piperazine-1-carboxamide The above compound (61 mg, 63%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3,5-difluorophenyl)piperazine.

¹H NMR (500 MHz, CDCl₃) δ 6.94 (s, 1H), 6.49 (t, J=8.4 Hz, 1H), 6.42-6.34 (m, 2H), 6.30 (tt, J=8.8 Hz, 2.1 Hz, 1H), 4.06 (s, 3H), 3.74-3.68 (m, 4H), 3.34-3.22 (m, 4H), 2.48 (s, 3H).

Example 28: 4-(3-Fluoro-5-(trifluoromethyl)phenyl)-N-(3-methoxy-6-methylfuro[2,3-b]pyrazin-2-yl)piperazine-1-carboxamide The above compound (92 mg, 85%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3-fluoro-5-(trifluoromethyl)phenyl)piperazine.

¹H NMR (500 MHz, CDCl₃) δ 7.01 (s, 1H), 6.69-6.59 (m, 1H), 6.42-6.34 (m, 2H), 6.30-6.12 (m, 1H), 4.06 (s, 3H), 3.74-3.68 (m, 4H), 3.34-3.22 (m, 4H), 2.48 (s, 3H).

Example 29: 4-(3,5-Bis(trifluoromethyl)phenyl)-N-(3-methoxy-6-methylfuro[2,3-b]pyrazin-2-yl)piperazine-1-carboxamide The above compound (108 mg, 90%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3,5-bis(trifluoromethyl)phenyl)piperazine.

¹H NMR (500 MHz, CDCl₃) δ 7.00 (s, 1H), 6.69-6.55 (m, 1H), 6.42-6.30 (m, 2H), 6.30-6.12 (m, 1H), 4.07 (s, 31-1), 3.74-3.69 (m, 4H), 3.34-3.19 (m, 4H), 2.48 (s, 3H).

Example 30: N-(3-Methoxy-6-methylfuro[2,3-b]pyrazin-2-yl)-4-(3-(trifluoromethoxy)phenyl)piperazine-1-carboxamide The above compound (77 mg, 71%) was obtained by carrying out the reaction in the same manner as in Step 8 of Example 21 using phenyl N-(3-methoxy-6-methyl-furo[2,3-b]pyrazin-2-yl)-N-phenoxycarbonylcarbamate and 1-(3-(trifluoromethoxy)phenyl)piperazine.

¹H NMR (500 MHz, CDCl₃) δ 7.72 (s, 1H), 7.33-7.28 (m, 1H), 7.03 (s, 1H), 6.86 (d, J=8.2 Hz, 1H), 6.75 (d, J=9.0 Hz, 2H), 4.07 (s, 3H), 3.74-3.69 (m, 4H), 3.34-3.19 (m, 4H), 2.48 (s, 3H).

Example 31: 4-(3,5-Dimethoxyphenyl)-N-(3-ethoxy-6-methylfuro[2,3-b]pyrazin-2-yl)piperazine-1-carboxamide The above compound (86 mg, 85%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3,5-dimethoxyphenyl)piperazine.

¹H NMR (500 MHz, CDCl₃) δ 7.02 (s, 1H), 6.49 (s, 1H), 6.14-5.98 (m, 3H), 4.48 (q, J=7.0 Hz, 2H), 3.78 (s, 3H), 3.74-3.54 (m, 4H), 3.29-3.13 (m, 4H), 2.46 (s, 3H), 1.45 (t, J=7.0 Hz, 3H).

Example 32: N-(3-Ethoxy-6-methylfuro[2,3-b]pyrazin-2-yl)-4-(3-methoxy-5-methylphenyl)piperazine-1-carboxamide The above compound (86 mg, 88%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3-methoxy-5-methylphenyl)piperazine.

¹H NMR (500 MHz, CDCl₃) δ 7.01 (s, 1H), 6.49 (s, 1H), 6.38 (s, 1H), 6.30 (s, 2H), 4.48 (q, J=7.0 Hz, 2H), 3.78 (s, 3H), 3.75-3.68 (m, 4H), 3.31-3.20 (m, 4H), 2.46 (s, 3H), 2.31 (s, 3H), 1.45 (t, J=7.0 Hz, 31-1).

Example 33: N-(3-Ethoxy-6-methylfuro[2,3-b]pyrazin-2-yl)-4-(3-fluoro-5-methoxyphenyl)piperazine-1-carboxamide The above compound (88 mg, 90%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3-fluoro-5-methoxyphenyl)piperazine.

¹H NMR (500 MHz, CDCl₃) δ 6.93 (s, 1H), 6.50 (d, J=1.0 Hz, 1H), 6.30-6.12 (m, 3H), 4.49 (q, J=7.1 Hz, 2H), 3.78 (s, 3H), 3.72 (dd, J=14.6 Hz, 9.5 Hz, 4H), 3.40-3.23 (m, 4H), 2.47 (d, J=0.8 Hz, 3H), 1.46 (t, J=7.1 Hz, 3H).

Example 34: 4-(3-(2-(Dimethylamino)ethoxy)-5-methoxyphenyl)-N-(3-ethoxy-6-methylfuro[2,3-b]pyrazin-2-yl)piperazine-1-carboxamide The above compound (74 mg, 65%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 2-(3-methoxy-5-(piperazine-1-yl)phenoxy)-N,N-dimethylethan-1-amine.

¹H NMR (500 MHz, CDCl₃) δ 7.02 (s, 1H), 6.49 (s, 1H), 6.38 (s, 1H), 6.28 (s, 2H), 4.69 (t, J=5.6 Hz, 2H), 4.47 (q, J=7.1 Hz, 2H), 3.78 (s, 3H), 3.75-3.68 (m, 4H), 3.31-3.20 (m, 4H), 2.31 (s, 3H), 1.45 (t, J=7.0 Hz, 3H), 2.80-3.10 (m, 2H), 2.46 (s, 9H).

Example 35: 4-(3,5-Dimethylphenyl)-N-(3-ethoxy-6-methylfuro[2,3-b]pyrazin-2-yl)piperazine-1-carboxamide The above compound (89 mg, 95%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3,5-dimethylphenyl)piperazine.

¹H NMR (500 MHz, CDCl₃) δ 6.98 (s, 1H), 6.58 (s, 3H), 6.50 (s, 1H), 4.49 (q, J=6.9 Hz, 2H), 3.65-3.75 (m, 4H), 3.18-28 (m, 4H), 2.44 (s, 3H), 2.29 (s, 6H), 1.46 (t, J=6.9 Hz, 3H).

Example 36: N-(3-Ethoxy-6-methylfuro[2,3-b]pyrazin-2-yl)-4-(3-fluoro-5-methylphenyl)piperazine-1-carboxamide The above compound (83 mg, 87%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3-fluoro-5-methylphenyl)piperazine.

¹H NMR (500 MHz, CDCl₃) δ 7.01 (s, 1H), 6.50 (d, J=5.5 Hz, 2H), 6.41 (d, J=9.9 Hz, 2H), 4.53-4.42 (m, 2H), 3.76-3.64 (m, 4H), 3.23 (dd, J=23.3 Hz, 18.4 Hz, 4H), 2.46 (s, 3H), 2.31 (s, 3H), 1.45 (t, J=7.0 Hz, 3H).

Example 37: 4-(3,5-Difluorophenyl)-N-(3-ethoxy-6-methylfuro[2,3-b]pyrazin-2-yl)piperazine-1-carboxamide The above compound (62 mg, 65%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3,5-difluorophenyl)piperazine.

¹H NMR (500 MHz, CDCl₃) δ 6.99 (s, 1H), 6.49 (s, 1H), 6.37 (d, J=8.5 Hz, 2H), 6.29 (dd, J=12.3 Hz, 5.3 Hz, 1H), 4.48 (q, J=7.0 Hz, 2H), 3.77-3.64 (m, 4H), 3.34-3.26 (m, 4H), 2.47 (s, 3H), 1.45 (t, J=7.1 Hz, 3H).

Example 38: N-(3-Ethoxy-6-methylfuro[2,3-b]pyrazin-2-yl)-4-(3-fluoro-5-(trifluoromethyl)phenyl)piperazine-1-carboxamide The above compound (81 mg, 75%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3-fluoro-5-(trifluoromethyl)phenyl)piperazine.

¹H NMR (500 MHz, CDCl₃) δ 7.01 (s, 1H), 6.61 (s, 1H), 6.37 (d, J=8.5 Hz, 2H), 6.29 (dd, J=12.3 Hz, 5.3 Hz, 1H), 4.47 (q, J=7.0 Hz, 2H), 3.77-3.68 (m, 4H), 3.34-3.26 (m, 4H), 2.47 (s, 3H), 1.44 J=7.1 Hz, 3H).

Example 39: 4-(3,5-Bis(trifluoromethyl)phenyl)-N-(3-ethoxy-6-methylfuro[2,3-b]pyrazin-2-yl)piperazine-1-carboxamide The above compound (108 mg, 91%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3,5-bis(trifluoromethyl)phenyl)piperazine.

$^1$H NMR (500 MHz, CDCl$_3$) δ 7.05 (s, 1H), 6.65 (s, 1H), 6.41 (d, J=8.5 Hz, 2H), 6.31 (dd, J=12.3 Hz, 5.3 Hz, 1H), 4.47 (q, J=7.0 Hz, 2H), 3.77-3.68 (m, 4H), 3.34-3.26 (m, 4H), 2.45 (s, 3H), 1.44 (t, J=7.1 Hz, 3H).

Example 40: N-(3-Ethoxy-6-methylfuro[2,3-b]pyrazin-2-yl)-4-(3-(trifluoromethoxy)phenyl)piperazine-1-carboxamide The above compound (80 mg, 75%) was obtained by carrying out the reaction in the same manner as in Step 8 of Example 21 using phenyl N-(3-ethoxy-6-methyl-furo[2,3-b]pyrazin-2-yl)-N-phenoxycarbonylcarbamate and 1-(3-(trifluoromethoxy)phenyl)piperazine.

$^1$H NMR (500 MHz, CDCl$_3$) δ 7.73 (s, 1H), 7.33-7.25 (m, 1H), 7.03 (s, 1H), 6.85 (d, J=8.2 Hz, 1H), 6.75 (d, J=9.0 Hz, 2H), 4.46 (q, J=7.0 Hz, 2H), 3.77-3.68 (m, 4H), 3.34-3.24 (m, 4H), 2.45 (s, 3H), 1.44 (t, J=7.1 Hz, 3H).

Example 41: N-(6-Chloro-3-methoxyfuro[2,3-b]pyrazin-2-yl)-4-(3,5-dimethoxyphenyl)piperazine-1-carboxamide

Step 1) Preparation of 2,6-dichlorofuro[2,3-b]pyrazine

After dissolving 2-chloro-6-(trimethylsilyl)furo[2,3-b]pyrazine (1.01 g, 4.47 mmol) in acetonitrile (30 mL), N-chlorosuccinimide (2.08 g, 15.63 mmol) and a silica gel were added and stirred at 80° C. for 12 hours. The reaction mixture was cooled to room temperature, filtered under reduced pressure using celite, and washed 3 times with dichloromethane (20 mL). The solvent was concentrated under reduced pressure and the remaining residue was purified on a silica gel column by chromatography. A mixed solvent of hexane and ethyl acetate (15:1, v/v) was used for elution, and then the title compound (0.32 g, 38%) was obtained.

$^1$H NMR (500 MHz, CDCl$_3$) δ 8.26 (s, 1H), 6.85 (s, 1H).

Step 2) Preparation of tert-butyl (6-chlorofuro[2,3-b]pyrazin-2-yl)carbamate The above compound (0.64 g, 45%) was obtained by carrying out the reaction in the same manner as in Step 5 of Example 1 using 2,6-dichlorofuro[2,3-b]pyrazine.

$^1$H NMR (500 MHz, CDCl$_3$) δ 8.75 (s, 1H), 7.28 (brs, 1H), 6.75 (s, 1H), 1.54 (s, 9H).

Step 3) Preparation of 6-chlorofuro[2,3-b]pyrazine-2-amine

The above compound (0.2 g, 50%) was obtained by carrying out the reaction in the same manner as in Step 6 of Example 1 using tert-butyl (6-chlorofuro[2,3-b]pyrazin-2-yl)carbamate.

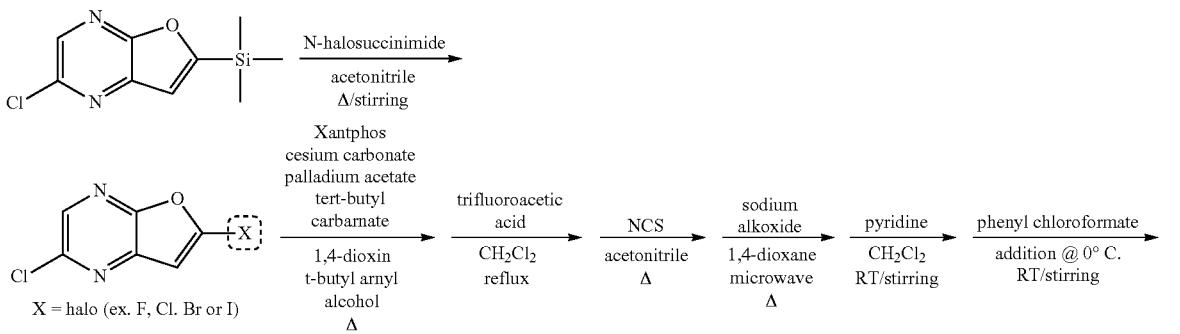

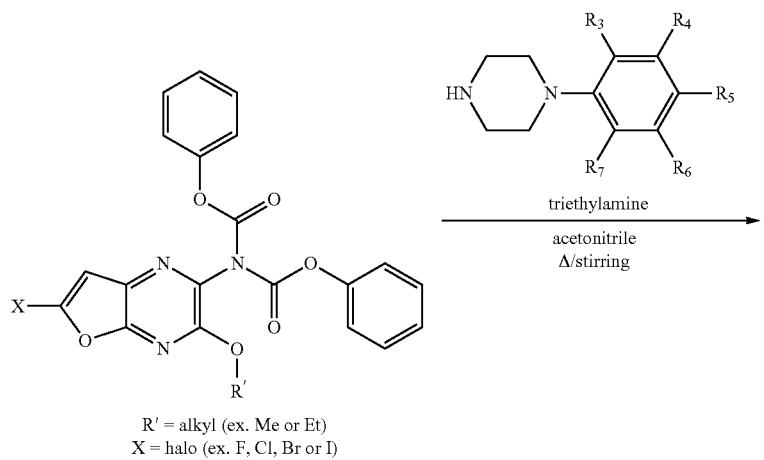

R' = alkyl (ex. Me or Et)
X = halo (ex. F, Cl, Br or I)

¹H NMR (500 MHz, CDCl₃) δ 7.82 (s, 1H), 6.63 (s, 1H), 4.42 (brs, 2H).

Step 4) Preparation of 3,6-dichlorofuro[2,3-b]pyrazine-2-amine

The above compound (0.17 g, 70%) was obtained by carrying out the reaction in the same manner as in Step 7 of Example 1 using 6-chlorofuro[2,3-b]pyrazine-2-amine.
¹H NMR (500 MHz, CDCl₃) δ 6.43 (s, 1H), 4.72 (brs, 2H).

Step 5) Preparation of 6-chloro-3-methoxyfuro[2,3-b]pyrazine-2-amine

The above compound (0.11 g, 65%) was obtained by carrying out the reaction in the same manner as in Step 8 of Example 1 using 3,6-dichlorofuro[2,3-b]pyrazine-2-amine.
¹H NMR (500 MHz, CDCl₃) δ 6.23 (s, 1H), 4.52 (brs, 2H), 4.05 (s, 3H).

Step 6) Preparation of phenyl N-(3-methoxy-6-chloro-furo[2,3-b]pyrazin-2-yl)-N-phenoxycarbonyl-carbamate The above compound (0.19 g, 78%) was obtained by carrying out the reaction in the same manner as in Step 9 of Example 1 using 6-chloro-3-methoxyfuro[2,3-b]pyrazine-2-amine.
¹H NMR (500 MHz, CDCl₃) δ 7.48 (t, J=7.8 Hz, 4H), 7.36-7.18 (m, 3H), 7.16-7.10 (m, 4H), 6.43 (s, 1H), 4.20 (s, 3H).

Step 7) Preparation of N-(6-chloro-3-methoxyfuro[2,3-b]pyrazin-2-yl)-4-(3,5-dimethoxyphenyl)piperazine-1-carboxamide The above compound (91 mg, 89%) was obtained by carrying out the reaction in the same manner as in Step 10 of Example 1 using phenyl N-(3-methoxy-6-chloro-furo[2,3-b]pyrazin-2-yl)-N-phenoxycarbonylcarbamate and 1-(3,5-dimethoxyphenyl)piperazine.
¹H NMR (500 MHz, CDCl₃) δ 6.90 (s, 1H), 6.52 (s, 1H), 6.11 (t, J=5.9 Hz, 2H), 6.07 (t, J=2.0 Hz, 1H), 4.06 (s, 3H), 3.78 (s, 6H), 3.72-3.59 (m, 4H), 3.28-3.17 (m, 4H).

Example 42: N-(6-Chloro-3-methoxyfuro[2,3-b]pyrazin-2-yl)-4-(3-methoxy-5-methylphenyl)piperazine-1-carboxamide The title compound (80 mg, 82%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3-methoxy-5-methylphenyl)piperazine.
¹H NMR (500 MHz, CDCl₃) δ 7.00 (s, 1H), 6.52 (s, 1H), 6.37 (s, 1H), 6.30 (s, 2H), 4.05 (s, 3H), 3.78 (s, 3H), 3.75-3.68 (m, 4H), 3.31-3.20 (m, 4H), 2.31 (s, 3H).

Example 43: N-(6-Chloro-3-methoxyfuro[2,3-b]pyrazin-2-yl)-4-(3-fluoro-5-methoxyphenyl)piperazine-1-carboxamide The title compound (91 mg, 92%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3-fluoro-5-methoxyphenyl)piperazine.
¹H NMR (500 MHz, CDCl₃) δ 6.95 (s, 1H), 6.51 (s, 1H), 6.35-6.28 (m, 3H), 4.06 (s, 3H), 3.78 (s, 3H), 3.65-3.55 (m, 4H), 3.32-3.22 (m, 4H).

Example 44: N-(6-Chloro-3-methoxyfuro[2,3-b]pyrazin-2-yl)-4-(3-(2-(dimethylamino)ethoxy)-5-methoxyphenyl)piperazine-1-carboxamide The title compound (82 mg, 71%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 2-(3-methoxy-5-(piperazine-1-yl)phenoxy)-N,N-dimethylethan-1-amine.
¹H NMR (500 MHz, CDCl₃) δ 6.81 (s, 1H), 6.51 (s, 1H), 6.29-6.22 (m, 3H), 4.69 (t, J=5.6 Hz, 2H), 4.05 (s, 3H), 3.78 (s, 3H), 3.75-3.65 (m, 4H), 3.32-3.22 (m, 4H), 2.80-3.15 (m, 2H), 2.45 (s, 6H).

Example 45: N-(6-Chloro-3-methoxyfuro[2,3-b]pyrazin-2-yl)-4-(3,5-dimethylphenyl)piperazine-1-carboxamide The title compound (81 mg, 86%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3,5-dimethylphenyl)piperazine.
¹H NMR (500 MHz, CDCl₃) δ 6.85 (s, 1H), 6.38 (s, 3H), 6.53 (s, 1H), 4.06 (s, 3H), 3.78-3.64 (m, 4H), 3.29-3.15 (m, 4H), 2.45 (s, 3H), 2.32 (s, 6H).

Example 46: N-(6-Chloro-3-methoxyfuro[2,3-b]pyrazin-2-yl)-4-(3-fluoro-5-methylphenyl)piperazine-1-carboxamide The title compound (82 mg, 86%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3-fluoro-5-methylphenyl)piperazine.
¹H NMR (500 MHz, CDCl₃) δ 6.91 (s, 1H), 6.51 (s, 2H), 6.42-6.38 (m, 2H), 4.06 (s, 3H), 3.72-3.65 (m, 4H), 3.31-3.15 (m, 4H), 2.48 (s, 3H).

Example 47: N-(6-Chloro-3-methoxyfuro[2,3-b]pyrazin-2-yl)-4-(3,5-difluorophenyl)piperazine-1-carboxamide The title compound (79 mg, 82%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3,5-difluorophenyl)piperazine.
¹H NMR (500 MHz, CDCl₃) δ 6.91 (s, 1H), 6.44 (t, J=8.4 Hz, 1H), 6.42-6.34 (m, 2H), 6.30 (tt, J=8.8 Hz, 2.1 Hz, 1H), 4.06 (s, 3H), 3.74-3.68 (m, 4H), 3.34-3.22 (m, 4H).

Example 48: N-(6-Chloro-3-methoxy-furo[2,3-b]pyrazin-2-yl)-4-(3-fluoro-5-(trifluoromethyl)phenyl)piperazine-1-carboxamide The title compound (84 mg, 78%) was obtained by carrying out the reaction in the same manner as in Step 7 of Example 41 using phenyl N-(3-methoxy-6-chloro-furo[2,3- b]pyrazin-2-yl)-N-phenoxycarbonylcarbamate and 1-(3-fluoro-5-(trifluoromethyl)phenyl)piperazine.
¹H NMR (500 MHz, CDCl₃) δ 7.01 (s, 1H), 6.69 (s, 1H), 6.42-6.34 (m, 2H), 6.30-6.12 (m, 1H), 4.05 (s, 3H), 3.74-3.68 (m, 4H), 3.34-3.22 (m, 4H).

Example 49: 4-(3,5-Bis(trifluoromethyl)phenyl)-N-(6-chloro-3-methoxy-furo[2,3-b]pyrazin-2-yl)piperazine-1-carboxamide The title compound (88 mg, 74%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3,5-bis(trifluoromethyl)phenyl)piperazine.
¹H NMR (500 MHz, CDCl₃) δ 7.05 (s, 1H), 6.69-6.52 (m, 1H), 6.42-6.30 (m, 21-1), 6.30-6.20 (m, 1H), 4.07 (s, 3H), 3.74-3.69 (m, 4H), 3.34-3.19 (m, 4H).

Example 50: N-(6-Chloro-3-methoxy-furo[2,3-b]pyrazin-2-yl)-4-(3-(trifluoromethoxy)phenyl)piperazine-1-carboxamide The title compound (75 mg, 70%) was obtained by carrying out the reaction in the same manner as in Step 7 of Example 41 using phenyl N-(3-methoxy-6-chloro-furo[2,3-b]pyrazin-2-yl)-N-phenoxycarbonylcarbamate and 1-(3-(trifluoromethoxy)phenyl)piperazine.
¹H NMR (500 MHz, CDCl₃) δ 7.01 (s, 1H), 7.33-7.28 (m, 1H), 7.03 (s, 1H), 6.86 (d, J=8.2 Hz, 1H), 6.75 (d, J=9.0 Hz, 2H), 4.05 (s, 3H), 3.74-3.69 (m, 4H), 3.34-3.19 (m, 4H).

Example 51: N-(6-Chloro-3-ethoxyfuro[2,3-b]pyrazin-2-yl)-4-(3,5-dimethoxyphenyl)piperazine-1-carboxamide The title compound (88 mg, 86%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3,5-dimethoxyphenyl)piperazine.
¹H NMR (500 MHz, CDCl₃) δ 6.91 (s, 1H), 6.52 (s, 1H), 6.15 (t, J=5.9 Hz, 2H), 6.06 (t, J=2.0 Hz, 1H), 4.45 (q, J=7.0 Hz, 2H), 3.77 (s, 6H), 3.72-3.59 (m, 4H), 3.28-3.17 (m, 4H), 1.42 (t, J=7.1 Hz, 3H).

Example 52: N-(6-Chloro-3-ethoxyfuro[2,3-b]pyrazin-2-yl)-4-(3-methoxy-5-methylphenyl)piperazine-1-carboxamide The title compound (88 mg, 90%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3-methoxy-5-methylphenyl)piperazine.
¹H NMR (500 MHz, CDCl₃) δ 6.98 (s, 1H), 6.51 (s, 1H), 6.37 (s, 1H), 6.25 (s, 2H), 4.43 (q, J=7.0 Hz, 2H), 3.78 (s, 3H), 3.75-3.68 (m, 4H), 3.31-3.20 (m, 4H), 2.21 (s, 3H), 1.41 (t, J=7.1 Hz, 3H).

Example 53: N-(6-Chloro-3-ethoxyfuro[2,3-b]pyrazin-2-yl)-4-(3-fluoro-5-methoxyphenyl)piperazine-1-carboxamide The title compound (91 mg, 92%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3-fluoro-5-methoxyphenyl)piperazine.
¹H NMR (500 MHz, CDCl₃) δ 6.95 (s, 1H), 6.55 (s, 1H), 6.35-6.28 (m, 3H), 4.50 (q, J=7.2 Hz, 2H), 4.16 (s, 3H), 3.65-3.53 (m, 4H), 3.32-3.21 (m, 4H), 1.42 (t, J=7.1 Hz, 3H).

Example 54: N-(6-Chloro-3-ethoxyfuro[2,3-b]pyrazin-2-yl)-4-(3-(2-(dimethylamino)ethoxy)-5-methoxyphenyl)piperazine-1-carboxamide The title compound (74 mg, 65%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 2-(3-methoxy-5-(piperazin-1-yl)phenoxy)-N,N-dimethylethan-1-amine.
¹H NMR (500 MHz, CDCl₃) δ 6.85 (s, 1H), 6.53 (s, 1H), 6.29-6.20 (m, 3H), 4.69 (t, J=5.6 Hz, 2H), 4.41 (q, J=7.0 Hz, 2H), 4.05 (s, 3H), 3.75-3.65 (m, 4H), 3.32-3.22 (m, 4H), 2.80-3.15 (m, 2H), 2.45 (s, 6H), 1.40 (t, J=7.1 Hz, 31-1).

Example 55: N-(6-Chloro-3-ethoxyfuro[2,3-b]pyrazin-2-yl)-4-(3,5-dimethylphenyl)piperazine-1-carboxamide The title compound (88 mg, 93%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3,5-dimethylphenyl)piperazine.
¹H NMR (500 MHz, CDCl₃) δ 6.83 (s, 1H), 6.35 (s, 3H), 6.53 (s, 1H), 4.40 (q, J=7.0 Hz, 2H), 3.78-3.64 (m, 4H), 3.29-3.15 (m, 4H), 2.32 (s, 6H), 1.39 (t, J=7.1 Hz, 3H).

Example 56: N-(6-Chloro-3-ethoxyfuro[2,3-b]pyrazin-2-yl)-4-(3-fluoro-5-methylphenyl)piperazine-1-carboxamide The title compound (86 mg, 90%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3-fluoro-5-methylphenyl)piperazine.
¹H NMR (500 MHz, CDCl₃) δ 6.91 (s, 1H), 6.51 (s, 2H), 6.42-6.38 (m, 21-1), 4.29 (q, J=7.2 Hz, 2H), 3.72-3.65 (m, 4H), 3.31-3.15 (m, 4H), 2.48 (s, 3H), 1.42 (t, J=7.1 Hz, 3H).

Example 57: N-(6-Chloro-3-ethoxyfuro[2,3-b]pyrazin-2-yl)-4-(3,5-difluorophenyl)piperazine-1-carboxamide The title compound (82 mg, 85%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3,5-difluorophenyl)piperazine.
¹H NMR (500 MHz, CDCl₃) δ 6.90 (s, 1H), 6.54-6.44 (m, 1H), 6.42-6.34 (m, 2H), 6.30 (tt, J=8.8 Hz, 2.1 Hz, 1H), 4.35 (q, J=7.0 Hz, 2H), 3.74-3.68 (m, 4H), 3.34-3.22 (m, 4H), 1.40 (t, J=7.1 Hz, 3H).

Example 58: N-(6-Chloro-3-ethoxyfuro[2,3-b]pyrazin-2-yl)-4-(3-fluoro-5-(trifluoromethyl)phenyl)piperazine-1-carboxamide The title compound (81 mg, 75%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3-fluoro-5-(trifluoromethyl)phenyl)piperazine.

$^1$H NMR (500 MHz, CDCl$_3$) δ 6.98 (s, 1H), 6.70 (s, 1H), 6.42-6.34 (m, 2H), 6.30-6.18 (m, 1H), 4.35 (q, J=7.0 Hz, 2H), 3.74-3.68 (m, 4H), 3.34-3.22 (m, 4H), 1.41 (t, J=7.2 Hz, 3H).

Example 59: 4-(3,5-Bis(trifluoromethyl)phenyl)-N-(6-chloro-3-ethoxyfuro[2,3-b]pyrazin-2-yl)piperazine-1-carboxamide The title compound (84 mg, 71%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3,5-bis(trifluoromethyl)phenyl)piperazine.

$^1$H NMR (500 MHz, CDCl$_3$) δ 7.00 (s, 1H), 6.69-6.55 (m, 1H), 6.42-6.30 (m, 2H), 6.30-6.20 (m, 1H), 4.35 (q, J=7.0 Hz, 2H), 4.00 (s, 3H), 3.74-3.69 (m, 4H), 3.34-3.19 (m, 4H), 1.42 (t, J=7.2 Hz, 3H).

Example 60: N-(6-Chloro-3-ethoxyfuro[2,3-b]pyrazin-2-yl)-4-(3-(trifluoromethoxy)phenyl)piperazine-1-carboxamide The title compound (73 mg, 68%) was obtained by carrying out the reaction in the same manner as in Step 7 of Example 41 using phenyl N-(3-ethoxy-6-chloro-furo[2,3-b]pyrazin-2-yl)-N-phenoxycarbonylcarbamate and 1-(3-(trifluoromethoxy)phenyl)piperazine.

$^1$H NMR (500 MHz, CDCl$_3$) δ 7.00 (s, 1H), 7.35-7.30 (m, 1H), 7.03 (s, 1H), 6.84 (d, J=8.2 Hz, 1H), 6.75-6.65 (m, 2H), 4.41 (q, J=7.0 Hz, 2H), 3.74-3.69 (m, 4H), 3.34-3.19 (m, 4H), 1.41 (t, J=7.2 Hz, 3H).

Experimental Example 1: Culture of Cancer Cell Line

The cell lines below were used in order to confirm the efficacy of the compounds synthesized in Examples 1 to 60. Human PANC-1 (pancreatic cancer) and MDA-MB-231 (breast cancer) cell lines were were obtained from the American Type Culture Collection (ATCC; Manassas, Va.); and HN31 (head and neck cancer) and UMRC2 (kidney cancer) cell lines were secured from the United States National Institutes of Health (Bethesda, Md.). The MDA-MB-231, UMRC2, HN31, and PANC-1 cell lines were cultured in Dulbecco modified Eagle medium (DMEM; Invitrogen, Carlsbad, Calif.) containing FBS (10%), HEPES (10 mM), penicillin (100 U/mL), and streptomycin (100 μg/mL). All cell lines were cultured in an incubator (37° C., 5% CO$_2$).

Experimental Example 2: Cell Growth Inhibition Experiment on Cancer Cell Line The 4-(aryl)-N-(3-alkoxyfuro[2,3-b]pyrazin-2-yl)-piperazine-1-carboxamide derivative compounds synthesized according to Examples 1 to 60 of the present invention were treated with various human tissue-derived cancer cell lines cultured according to Experimental Example 1, and thus the inhibitory effect of the growth of human cancer cells was confirmed. The cell growth inhibition experiment was conducted using the sulforhodamine B (SRB) technique (Skehan et al., J. National Cancer Institute, 1990, 82: 1107-1112). Specifically, each cell line was seeded in a 96-well plate at a density of 2 to 3×10$^3$ cells/well, cultured overnight, and then treated with the 4-(aryl)-N-(3-alkoxyfuro[2,3-b]pyrazin-2-yl)-piperazine-1-carboxamide derivative compounds of the present invention. The experiment was repeated 3 times for each compound. Cells treated with each compound were additionally incubated for 96 hours, fixed with 10% trichloroacetic acid (TCA), and then left at 4° C. for 1 hour. The resultant was washed 3 times with distilled water. Thereafter, each cell was treated with 0.4% sulforhodamine B dissolved in 1% acetic acid, stained for 30 minutes, and then washed 4 times with 1% acetic acid. The resultant was dried in the air. After shaking the resultant in Tris solution (10 mM) for 5 minutes, the absorbance was measured at 530 nm using a Benchmark Plus Microplate reader (Bio-Rad Laboratories, Hercules, Calif.).

In order to convert the OD$_{530}$ value to the number of viable cells per each well, the measured OD$_{530}$ value was compared to the standard OD$_{530}$-vs.-cell number curve of each cell line. The percent survival was calculated using the following formula:

% survival=$N_{live\ cells}$(test)/$N_{live\ cells}$(control)×100

The IC$_{50}$ values for the compounds of Examples 1 to 60, listed in Table 1 above, were derived and are summarized in Tables 12 to 19 below, which confirmed the possibility of using the compounds as anti-proliferative agents. As shown in Tables 12 to 19 below, it was confirmed that the 4-(aryl)-N-(3-alkoxyfuro[2,3-b]pyrazin-2-yl)-piperazine-1-carboxamide derivative compounds according to Examples 1 to 60 of the present invention were all excellent anti-proliferative agents with IC$_{50}$ values of less than 2.50 μM, or as low as 0.02 μM.

TABLE 12

| | IC$_{50}$ (μM) for cancer cell line | | | | | | | | |
|---|---|---|---|---|---|---|---|---|---|
| Example # | MDA-MB-231 | UMRC2 | PANC-1 | HN31 | A549 | HEK293 | HUVEC | HT29 | SK-OV-3 |
| 1 | 0.12 | 0.03 | 0.53 | 0.27 | 1.13 | 0.63 | 0.12 | 0.31 | 0.27 |
| 2 | 0.26 | 0.38 | 0.45 | 0.49 | 0.23 | 1.93 | 0.91 | 0.62 | 0.82 |
| 3 | 0.24 | 0.06 | 0.56 | 0.71 | 2.11 | <2.50 | <2.50 | 1.53 | 0.85 |
| 4 | 1.13 | 0.54 | 0.68 | 1.54 | <2.50 | <2.50 | 1.25 | <2.50 | <2.50 |
| 5 | 1.12 | 1.72 | 1.32 | 2.35 | <2.50 | <2.50 | <2.50 | <2.50 | <2.50 |

TABLE 13

| 6 | 1.13 | 1.21 | 0.98 | 1.98 | 1.78 | 1.83 | <2.50 | <2.50 | <2.50 |
|---|---|---|---|---|---|---|---|---|---|
| 7 | 1.78 | 1.78 | 1.89 | <2.50 | <2.50 | <2.50 | <2.50 | <2.50 | <2.50 |
| 8 | 0.98 | 0.88 | 1.98 | <2.50 | <2.50 | <2.50 | <2.50 | <2.50 | <2.50 |
| 9 | <2.50 | <2.50 | <2.50 | <2.50 | <2.50 | <2.50 | <2.50 | <2.50 | <2.50 |
| 10 | 1.02 | 1.13 | 0.68 | 0.28 | 1.14 | 0.56 | 1.36 | 1.27 | 1.23 |
| 11 | 0.07 | 0.07 | 0.24 | 0.41 | 1.51 | 0.65 | 0.07 | 1.31 | 1.27 |
| 12 | 0.05 | 0.14 | 0.24 | 0.33 | 1.28 | 1.55 | 0.27 | 1.30 | 1.29 |
| 13 | 0.16 | 0.26 | 0.65 | 0.72 | <2.50 | <2.50 | <2.50 | <2.50 | <2.50 |

TABLE 14

| 14 | 0.34 | 0.68 | 1.23 | 0.65 | 1.85 | <2.50 | <2.50 | <2.50 | <2.50 |
| 15 | 0.24 | 0.25 | 1.12 | 0.78 | <2.50 | <2.50 | <2.50 | <2.50 | <2.50 |
| 16 | 0.24 | 0.44 | <2.50 | <2.50 | <2.50 | <2.50 | <2.50 | <2.50 | <2.50 |
| 17 | 0.24 | 1.65 | <2.50 | <2.50 | <2.50 | <2.50 | <2.50 | <2.50 | <2.50 |
| 18 | 0.44 | 0.24 | <2.50 | <2.50 | <2.50 | <2.50 | <2.50 | <2.50 | <2.50 |
| 19 | 0.34 | 0.68 | 1.23 | 0.36 | 0.44 | 1.23 | 0.68 | 0.71 | <2.50 |
| 20 | 0.25 | 1.63 | 0.36 | 0.36 | 0.24 | 0.12 | 0.21 | 0.62 | 0.22 |

TABLE 15

| 21 | 0.44 | 1.74 | 2.12 | <2.50 | 1.63 | 1.25 | <2.50 | 1.85 | 1.85 |
| 22 | 0.52 | 0.21 | 0.63 | 0.44 | 2.21 | 1.12 | 1.36 | 1.12 | 1.36 |
| 23 | 0.36 | 0.44 | 0.44 | 0.28 | 0.63 | 0.35 | 0.45 | 0.28 | 0.36 |
| 24 | 0.12 | 0.36 | 0.44 | <2.50 | 0.87 | 0.25 | <2.50 | 0.36 | 0.12 |
| 25 | 0.15 | <2.50 | 0.08 | 0.17 | 0.22 | 0.36 | 0.13 | 0.25 | 0.63 |
| 26 | 1.32 | 1.56 | <2.50 | <2.50 | <2.50 | <2.50 | <2.50 | <2.50 | <2.50 |
| 27 | 0.56 | 1.13 | <2.50 | <2.50 | <2.50 | <2.50 | <2.50 | <2.50 | <2.50 |
| 28 | <2.50 | <2.50 | <2.50 | <2.50 | <2.50 | <2.50 | <2.50 | <2.50 | <2.50 |

TABLE 16

| 29 | <2.50 | <2.50 | <2.50 | <2.50 | <2.50 | <2.50 | <2.50 | <2.50 | <2.50 |
| 30 | 0.68 | 0.63 | 0.54 | 1.32 | 0.25 | 0.58 | 1.12 | 1.12 | 1.12 |
| 31 | 0.12 | 0.36 | 0.44 | 1.63 | 1.25 | 0.24 | <2.50 | <2.50 | <2.50 |
| 32 | 0.44 | 0.52 | 0.32 | 1.63 | 1.39 | 1.12 | <2.50 | <2.50 | <2.50 |
| 33 | 0.15 | 0.21 | 0.24 | 0.31 | 0.41 | 0.51 | <2.50 | <2.50 | <2.50 |
| 34 | 0.36 | 1.21 | 0.44 | 1.02 | 0.68 | 0.44 | <2.50 | <2.50 | <2.50 |
| 35 | 0.24 | 0.54 | 0.43 | 0.44 | 1.02 | 1.12 | <2.50 | <2.50 | <2.50 |

TABLE 17

| 36 | 0.45 | 0.36 | 0.12 | 0.36 | 1.32 | 1.32 | 1.12 | 1.12 | 1.12 |
| 37 | 0.15 | 0.36 | 0.51 | 0.68 | 0.44 | 1.63 | 1.25 | 1.28 | 2.13 |
| 38 | <2.50 | <2.50 | <2.50 | <2.50 | <2.50 | <2.50 | <2.50 | <2.50 | <2.50 |
| 39 | <2.50 | <2.50 | <2.50 | <2.50 | <2.50 | <2.50 | <2.50 | <2.50 | <2.50 |
| 40 | <2.50 | <2.50 | <2.50 | <2.50 | <2.50 | <2.50 | <2.50 | <2.50 | <2.50 |
| 41 | 0.51 | 0.32 | 0.36 | 0.68 | 1.87 | 1.66 | 1.73 | 1.87 | <2.50 |
| 42 | 0.36 | 1.68 | 1.23 | 1.68 | 1.87 | 1.37 | 1.47 | 1.87 | <2.50 |
| 43 | 0.21 | 0.32 | 0.15 | 0.68 | 0.36 | 1.32 | 1.77 | 1.59 | 2.13 |
| 44 | 0.43 | 0.38 | 0.61 | 0.53 | 0.36 | 0.71 | 0.66 | 0.87 | <2.50 |

TABLE 18

| 45 | 0.69 | 0.32 | 0.68 | 1.68 | 1.81 | 2.01 | <2.50 | <2.50 | <2.50 |
| 46 | 1.68 | 1.35 | 1.94 | 1.83 | <2.50 | <2.50 | <2.50 | <2.50 | <2.50 |
| 47 | 0.43 | 0.68 | 0.41 | 0.68 | 0.57 | 0.63 | 1.87 | 1.92 | 1.93 |
| 43 | 0.12 | 0.36 | 0.44 | 0.57 | <2.50 | <2.50 | <2.50 | <2.50 | <2.50 |
| 49 | 0.32 | 1.03 | 1.68 | 1.17 | <2.50 | <2.50 | <2.50 | <2.50 | <2.50 |
| 50 | <2.50 | <2.50 | <2.50 | <2.50 | <2.50 | <2.50 | <2.50 | <2.50 | <2.50 |
| 51 | 0.32 | 1.68 | 1.58 | 1.45 | <2.50 | <2.50 | <2.50 | <2.50 | <2.50 |
| 52 | 1.18 | 0.68 | 1.68 | 1.36 | 1.87 | 1.74 | 1.62 | <2.50 | <2.50 |

TABLE 19

| 53 | 0.48 | 0.32 | 0.56 | 0.45 | 1.68 | 1.98 | 1.88 | 1.67 | 1.91 |
| 54 | 1.68 | 1.32 | 1.88 | 1.78 | 1.86 | 1.65 | 1.75 | <2.50 | <2.50 |
| 55 | 0.32 | 0.68 | 1.68 | 1.75 | <2.50 | <2.50 | <2.50 | <2.50 | <2.50 |
| 56 | 0.36 | 0.87 | 1.68 | 1.75 | <2.50 | <2.50 | <2.50 | <2.50 | <2.50 |
| 57 | <2.50 | <2.50 | <2.50 | <2.50 | <2.50 | <2.50 | <2.50 | <2.50 | <2.50 |
| 58 | <2.50 | <2.50 | <2.50 | <2.50 | <2.50 | <2.50 | <2.50 | <2.50 | <2.50 |
| 59 | 1.68 | 1.87 | 1.98 | <2.50 | <2.50 | <2.50 | <2.50 | <2.50 | <2.50 |

What is claimed is:

1. A compound represented by the following Formula 1 or a pharmaceutically acceptable salt thereof:

[Formula 1]

wherein $R_1$ is hydrogen, linear or branched $C_{1-6}$ alkyl, or halogen;

$R_2$ is linear or branched $C_{1-6}$ alkyl; and $R_3$ to $R_7$ each independently represent hydrogen, halogen, linear or branched $C_{1-6}$ alkyl, linear or branched $C_{1-6}$ haloalkyl, $C_{1-6}$ alkoxy, $C_{1-6}$ haloalkoxy, ($C_{1-6}$ alkyl)amino($C_{1-6}$ alkoxy), or di($C_{1-6}$ alkyl)amino($C_{1-6}$ alkoxy).

2. The compound of claim 1 or pharmaceutically acceptable salt thereof, wherein $R_1$ is hydrogen, linear or branched $C_{1-6}$ alkyl, or halogen;

$R_2$ is linear or branched $C_{1-6}$ alkyl;

$R_3$, $R_5$, and $R_7$ are all hydrogen; and $R_4$ and $R_6$ are the same or different from each other, and each independently represent hydrogen, halogen, linear or branched $C_{1-6}$ alkyl, linear or branched $C_{1-6}$ haloalkyl, $C_{1-6}$ alkoxy, $C_{1-6}$ haloalkoxy, ($C_{1-6}$ alkyl) amino($C_{1-6}$ alkoxy), or di($C_{1-6}$ alkyl)amino ($C_{1-6}$ alkoxy).

3. The compound of claim 1 or pharmaceutically acceptable salt thereof, wherein $R_1$ is hydrogen, methyl, or chloro.

4. The compound of claim 1 or pharmaceutically acceptable salt thereof, wherein $R_2$ is methyl or ethyl.

5. The compound of claim 1 or pharmaceutically acceptable salt thereof, wherein $R_3$ to $R_7$ each independently represent hydrogen, fluoro, methyl, trifluoromethyl, methoxy, trifluoromethoxy, or N,N-dimethylaminoethoxy.

6. The compound of claim 5 or pharmaceutically acceptable salt thereof, wherein $R_3$, $R_5$, and $R_7$ are all hydrogen.

7. The compound of claim 5 or pharmaceutically acceptable salt thereof, wherein $R_4$ and $R_6$ are the same or different from each other, and each independently represent hydrogen, fluoro, methyl, trifluoromethyl, methoxy, trifluoromethoxy, or N,N-dimethylaminoethoxy.

8. The compound of claim 1 or pharmaceutically acceptable salt thereof, wherein $R_1$ is hydrogen, methyl, or chloro;

$R_2$ is methyl or ethyl;

$R_3$, $R_5$, and $R_7$ are all hydrogen; and $R_4$ and $R_6$ are the same or different from each other, and each independently represent hydrogen, fluoro, methyl, trifluoromethyl, methoxy, trifluoromethoxy, or N,N-dimethylaminoethoxy.

9. The compound of claim 1 or pharmaceutically acceptable salt thereof, wherein the compound is selected from the group consisting of 1) 4-(3,5-dimethoxyphenyl)-N-(3-methoxyfuro[2,3-b]pyrazin-2-yl)piperazine-1-carboxamide,
2) 4-(3-methoxy-5-methylphenyl)-N-(3-methoxyfuro[2,3-b]pyrazin-2-yl)piperazine-1-carboxamide,
3) 4-(3-fluoro-5-methoxyphenyl)-N-(3-methoxyfuro[2,3-b]pyrazin-2-yl)piperazine-1-carboxamide,
4) 4-(3-(2-(dimethylamino)ethoxy)-5-methoxyphenyl)-N-(3-methoxyfuro[2,3-b]pyrazin-2-yl)piperazine-1-carboxamide,
5) 4-(3,5-dimethylphenyl)-N-(3-methoxyfuro[2,3-b]pyrazin-2-yl)piperazine-1-carboxamide,
6) 4-(3-fluoro-5-methylphenyl)-N-(3-methoxyfuro[2,3-b]pyrazin-2-yl)piperazine-1-carboxamide,
7) 4-(3,5-difluorophenyl)-N-(3-methoxyfuro[2,3-b]pyrazin-2-yl)piperazine-1-carboxamide,
8) 4-(3-fluoro-5-(trifluoromethyl)phenyl)-N-(3-methoxyfuro[2,3-b]pyrazin-2-yl)piperazine-1-carboxamide,
9) 4-(3,5-bis(trifluoromethyl)phenyl)-N-(3-methoxyfuro[2,3-b]pyrazin-2-yl)piperazine-1-carboxamide,
10) N-(3-methoxyfuro[2,3-b]pyrazin-2-yl)-4-(3-(trifluoromethoxy)phenyl)piperazine-1-carboxamide,
11) 4-(3,5-dimethoxyphenyl)-N-(3-ethoxyfuro[2,3-b]pyrazin-2-yl)piperazine-1-carboxamide,
12) N-(3-ethoxyfuro[2,3-b]pyrazin-2-yl)-4-(3-methoxy-5-methylphenyl)piperazine-1-carboxamide,
13) N-(3-ethoxyfuro[2,3-b]pyrazin-2-yl)-4-(3-fluoro-5-methoxyphenyl)piperazine-1-carboxamide,
14) 4-(3-(2-(dimethylamino)ethoxy)-5-methoxyphenyl)-N-(3-ethoxyfuro[2,3-b]pyrazin-2-yl)piperazine-1-carboxamide,
15) 4-(3,5-dimethylphenyl)-N-(3-ethoxyfuro[2,3-b]pyrazin-2-yl)piperazine-1-carboxamide,
16) N-(3-ethoxyfuro[2,3-b]pyrazin-2-yl)-4-(3-fluoro-5-methylphenyl)piperazine-1-carboxamide,
17) 4-(3,5-difluorophenyl)-N-(3-ethoxyfuro[2,3-b]pyrazin-2-yl)piperazine-1-carboxamide,
18) N-(3-ethoxyfuro[2,3-b]pyrazin-2-yl)-4-(3-fluoro-5-(trifluoromethyl)phenyl)piperazine-1-carboxamide,
19) 4-(3,5-bis(trifluoromethyl)phenyl)-N-(3-ethoxyfuro[2,3-b]pyrazin-2-yl)piperazine-1-carboxamide,
20) N-(3-ethoxyfuro[2,3-b]pyrazin-2-yl)-4-(3-(trifluoromethoxy)phenyl)piperazine-1-carboxamide,
21) 4-(3,5-dimethoxyphenyl)-N-(3-methoxy-6-methylfuro[2,3-b]pyrazin-2-yl)piperazine-1-carboxamide,
22) 4-(3-methoxy-5-methylphenyl)-N-(3-methoxy-6-methylfuro[2,3-b]pyrazin-2-yl)piperazine-1-carboxamide,
23) 4-(3-fluoro-5-methoxyphenyl)-N-(3-methoxy-6-methylfuro[2,3-b]pyrazin-2-yl)piperazine-1-carboxamide,
24) 4-(3-(2-(dimethylamino)ethoxy)-5-methoxyphenyl)-N-(3-methoxy-6-methylfuro[2,3-b]pyrazin-2-yl)piperazine-1-carboxamide,
25) 4-(3,5-dimethylphenyl)-N-(3-methoxy-6-methylfuro[2,3-b]pyrazin-2-yl)piperazine-1-carboxamide,
26) 4-(3-fluoro-5-methylphenyl)-N-(3-methoxy-6-methylfuro[2,3-b]pyrazin-2-yl)piperazine-1-carboxamide,
27) 4-(3,5-difluorophenyl)-N-(3-methoxy-6-methylfuro[2,3-b]pyrazin-2-yl)piperazine-1-carboxamide,
28) 4-(3-fluoro-5-(trifluoromethyl)phenyl)-N-(3-methoxy-6-methylfuro[2,3-b]pyrazin-2-yl)piperazine-1-carboxamide,
29) 4-(3,5-bis(trifluoromethyl)phenyl)-N-(3-methoxy-6-methylfuro[2,3-b]pyrazin-2-yl)piperazine-1-carboxamide,
30) N-(3-methoxy-6-methylfuro[2,3-b]pyrazin-2-yl)-4-(3-(trifluoromethoxy)phenyl)piperazine-1-carboxamide,
31) 4-(3,5-dimethoxyphenyl)-N-(3-ethoxy-6-methylfuro[2,3-b]pyrazin-2-yl)piperazine-1-carboxamide,
32) N-(3-ethoxy-6-methylfuro[2,3-b]pyrazin-2-yl)-4-(3-methoxy-5-methylphenyl)piperazine-1-carboxamide,
33) N-(3-ethoxy-6-methylfuro[2,3-b]pyrazin-2-yl)-4-(3-fluoro-5-methoxyphenyl)piperazine-1-carboxamide,
34) 4-(3-(2-(dimethylamino)ethoxy)-5-methoxyphenyl)-N-(3-ethoxy-6-methylfuro[2,3-b]pyrazin-2-yl)piperazine-1-carboxamide,
35) 4-(3,5-dimethylphenyl)-N-(3-ethoxy-6-methylfuro[2,3-b]pyrazin-2-yl)piperazine-1-carboxamide,
36) N-(3-ethoxy-6-methylfuro[2,3-b]pyrazin-2-yl)-4-(3-fluoro-5-methylphenyl)piperazine-1-carboxamide,
37) 4-(3,5-difluorophenyl)-N-(3-ethoxy-6-methylfuro[2,3-b]pyrazin-2-yl)piperazine-1-carboxamide,
38) N-(3-ethoxy-6-methylfuro[2,3-b]pyrazin-2-yl)-4-(3-fluoro-5-(trifluoromethyl)phenyl)piperazine-1-carboxamide,
39) 4-(3,5-bis(trifluoromethyl)phenyl)-N-(3-ethoxy-6-methylfuro[2,3-b]pyrazin-2-yl)piperazine-1-carboxamide,
40) N-(3-ethoxy-6-methylfuro[2,3-b]pyrazin-2-yl)-4-(3-(trifluoromethoxy)phenyl)piperazine-1-carboxamide,
41) N-(6-chloro-3-methoxyfuro[2,3-b]pyrazin-2-yl)-4-(3,5-dimethoxyphenyl)piperazine-1-carboxamide,
42) N-(6-chloro-3-methoxyfuro[2,3-b]pyrazin-2-yl)-4-(3-methoxy-5-methylphenyl)piperazine-1-carboxamide,
43) N-(6-chloro-3-methoxyfuro[2,3-b]pyrazin-2-yl)-4-(3-fluoro-5-methoxyphenyl)piperazine-1-carboxamide,
44) N-(6-chloro-3-methoxyfuro[2,3-b]pyrazin-2-yl)-4-(3-(2-(dimethylamino)ethoxy)-5-methoxyphenyl)piperazine-1-carboxamide,
45) N-(6-chloro-3-methoxyfuro[2,3-b]pyrazin-2-yl)-4-(3,5-dimethylphenyl)piperazine-1-carboxamide,
46) N-(6-chloro-3-methoxyfuro[2,3-b]pyrazin-2-yl)-4-(3-fluoro-5-methylphenyl)piperazine-1-carboxamide,
47) N-(6-chloro-3-methoxyfuro[2,3-b]pyrazin-2-yl)-4-(3,5-difluorophenyl)piperazine-1-carboxamide,
48) N-(6-chloro-3-methoxy-furo[2,3-b]pyrazin-2-yl)-4-(3-fluoro-5-(trifluoromethyl)phenyl)piperazine-1-carboxamide,
49) 4-(3,5-bis(trifluoromethyl)phenyl)-N-(6-chloro-3-methoxy-furo[2,3-b]pyrazin-2-yl)piperazine-1-carboxamide,
50) N-(6-chloro-3-methoxy-furo[2,3-b]pyrazin-2-yl)-4-(3-(trifluoromethoxy)phenyl)piperazine-1-carboxamide,
51) N-(6-chloro-3-ethoxyfuro[2,3-b]pyrazin-2-yl)-4-(3,5-dimethoxyphenyl)piperazine-1-carboxamide,
52) N-(6-chloro-3-ethoxyfuro[2,3-b]pyrazin-2-yl)-4-(3-methoxy-5-methylphenyl)piperazine-1-carboxamide,
53) N-(6-chloro-3-ethoxyfuro[2,3-b]pyrazin-2-yl)-4-(3-fluoro-5-methoxyphenyl)piperazine-1-carboxamide,
54) N-(6-chloro-3-ethoxyfuro[2,3-b]pyrazin-2-yl)-4-(3-(2-(dimethylamino)ethoxy)-5-methoxyphenyl)piperazine-1-carboxamide,
55) N-(6-chloro-3-ethoxyfuro[2,3-b]pyrazin-2-yl)-4-(3,5-dimethylphenyl)piperazine-1-carboxamide,
56) N-(6-chloro-3-ethoxyfuro[2,3-b]pyrazin-2-yl)-4-(3-fluoro-5-methylphenyl)piperazine-1-carboxamide,
57) N-(6-chloro-3-ethoxyfuro[2,3-b]pyrazin-2-yl)-4-(3,5-difluorophenyl)piperazine-1-carboxamide, 58) N-(6-chloro-3-ethoxyfuro[2,3-b]pyrazin-2-yl)-4-(3-fluoro-5-(trifluoromethyl)phenyl)piperazine-1-carboxamide,
59) 4-(3,5-bis(trifluoromethyl)phenyl)-N-(6-chloro-3-ethoxyfuro[2,3-b]pyrazin-2-yl)piperazine-1-carboxamide, and
60) N-(6-chloro-3-ethoxyfuro[2,3-b]pyrazin-2-yl)-4-(3-(trifluoromethoxy)phenyl)piperazine-1-carboxamide.

10. A method for preparing a compound represented by the following Formula 1, comprising:
  a first step of preparing a compound represented by the following Formula 3 from a compound represented by the following Formula 2; and
  a second step of preparing the compound represented by the following Formula 1 by reacting the compound represented by the following Formula 3 with a compound represented by the following Formula 4:

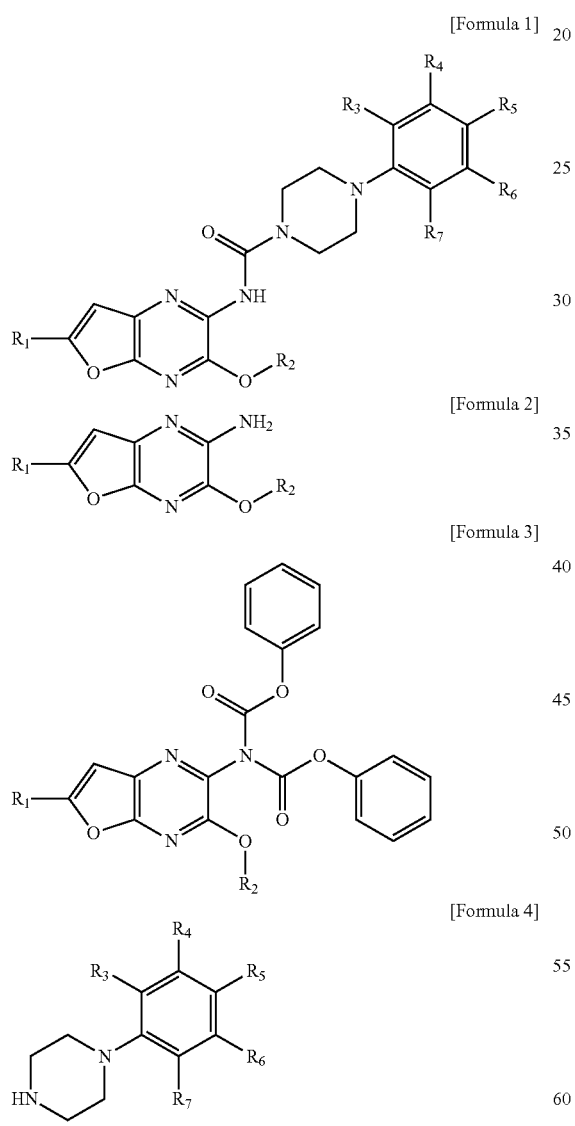

wherein
R$_1$ is hydrogen, linear or branched C$_{1-6}$ alkyl, or halogen;
R$_2$ is linear or branched C$_{1-6}$ alkyl; and
R$_3$ to R$_7$ each independently represent hydrogen, halogen, linear or branched C$_{1-6}$ alkyl, linear or branched C$_{1-6}$ haloalkyl, C$_{1-6}$ alkoxy, C$_{1-6}$ haloalkoxy, (C$_{1-6}$ alkyl)amino(C$_{1-6}$ alkoxy), or di(C$_{1-6}$ alkyl)amino(C$_{1-6}$ alkoxy).

11. The method of claim 10, wherein the compound represented by Formula 2 is synthesized from 2-((4-methoxybenzyl)amino)acetonitrile or a salt thereof.

12. The method of claim 10, wherein the compound represented by Formula 2 is synthesized by:
  i) a step of carrying out a cyclization reaction of a compound represented by the following Formula 5 with oxalyl chloride to obtain a compound represented by the following Formula 6;
  ii) a step of substituting the chloro group in the compound represented by Formula 6 with trimethylsilylethynyl or propynyl group to obtain a compound represented by the following Formula 7;
  iii) a step of carrying out a cyclization reaction of the compound represented by Formula 7 and substituting trimethylsilyl or methyl group in the compound obtained from the cyclization reaction, with R$_1$ group, to obtain a compound represented by the following Formula 8;
  iv) a step of substituting the chloro group in the compound represented by Formula 8 with (tert-butoxycarbonyl)amino group to obtain a compound represented by the following Formula 9;
  v) a step of removing the tert-butyl carboxyl from the compound represented by Formula 9 to obtain a compound represented by the following Formula 10;
  vi) a step of halogenating the compound represented by Formula 10 to obtain a compound represented by the following Formula 11; and
  vii) a step of substituting the halogen on the pyrazine ring of the compound represented by Formula 11 with a C$_{1-6}$ alkoxy group:

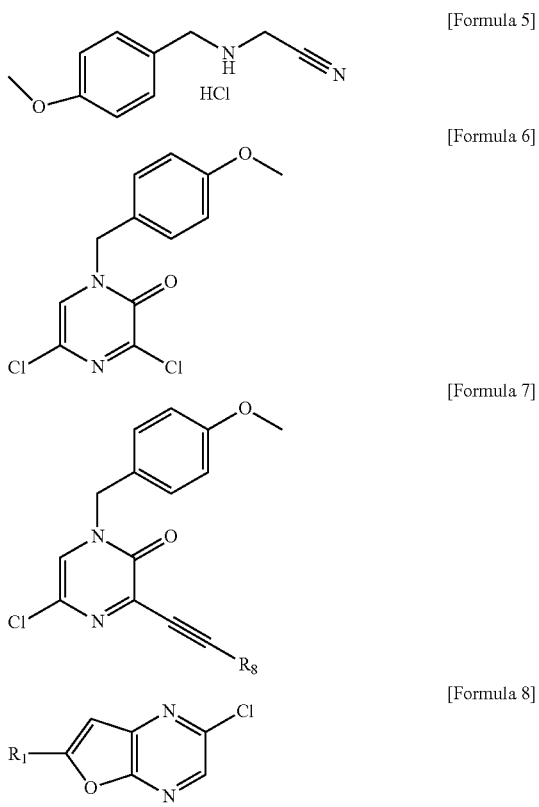

-continued

[Formula 9]

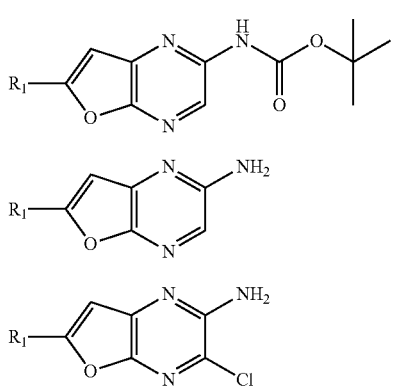

[Formula 10]

[Formula 11]

wherein

R$_1$ is hydrogen, linear or branched C$_{1-6}$ alkyl, or halogen; and

R$_8$ is trimethylsilyl or methyl.

13. The method of claim 12, wherein if R$_8$ is trimethylsilyl, step iii) further comprises a step of carrying out a cyclization reaction of the compound of Formula 7 to obtain a compound represented by the following Formula 12 as an intermediate:

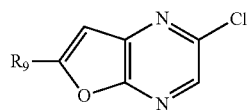

[Formula 12]

wherein R$_9$ is trimethylsilyl.

14. The method of claim 13, wherein step iii) further comprises a step of removing or halogenating the trimethylsilyl of the compound represented by Formula 12.

15. A method for treating a cancer, comprising providing a subject with a compound:

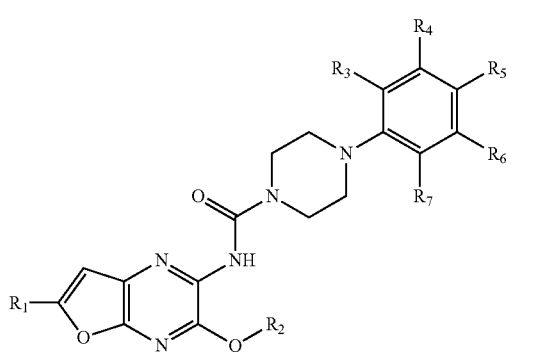

[Formula 1]

wherein

R$_1$ is hydrogen, linear or branched C$_{1-6}$ alkyl, or halogen;

R$_2$ is linear or branched C$_{1-6}$ alkyl; and

R$_3$ to R$_7$ each independently represent hydrogen, halogen, linear or branched C$_{1-6}$ alkyl, linear or branched C$_{1-6}$ haloalkyl, C$_{1-6}$ alkoxy, C$_{1-6}$ haloalkoxy, (C$_{1-6}$ alkyl)amino(C$_{1-6}$ alkoxy), or di(C$_{1-6}$ alkyl)amino(C$_{1-6}$ alkoxy), or the pharmaceutically acceptable salt thereof as an active ingredient.

16. The method of claim 15, wherein the treatment of cancer is achieved by inhibiting proliferation of cancer cells and inducing apoptosis thereof.

17. The method of claim 15, wherein the cancer is colon cancer, breast cancer, pancreatic cancer, head and neck cancer, kidney cancer, lung cancer, colorectal adenocarcinoma, or other adenocarcinoma.

* * * * *